United States Patent
Von Stein et al.

(10) Patent No.: US 11,771,428 B2
(45) Date of Patent: Oct. 3, 2023

(54) ACTUATION SHAFT RETENTION MECHANISM FOR SURGICAL STAPLER

(71) Applicant: Applied Medical Resources Corporation, Rancho Santa Margarita, CA (US)

(72) Inventors: Jonathan Von Stein, Rancho Santa Margarita, CA (US); Kimball B. McGinley, Rancho Santa Margarita, CA (US); Robert Bradshaw, Rancho Santa Margarita, CA (US); Alan Bylund, Rancho Santa Margarita, CA (US); Christian A. Halvorsen, Rancho Santa Margarita, CA (US); Jonathan R. Nash, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 19 days.

(21) Appl. No.: 17/514,358

(22) Filed: Oct. 29, 2021

(65) Prior Publication Data
US 2022/0133317 A1    May 5, 2022

Related U.S. Application Data

(60) Provisional application No. 63/107,112, filed on Oct. 29, 2020.

(51) Int. Cl.
*A61B 17/072* (2006.01)
*A61B 17/00* (2006.01)

(52) U.S. Cl.
CPC ...... *A61B 17/07207* (2013.01); *A61B 2017/0046* (2013.01); *A61B 2017/00398* (2013.01)

(58) Field of Classification Search
CPC .... A61B 17/07207; A61B 2017/00398; A61B 2017/0046
(Continued)

(56) References Cited

U.S. PATENT DOCUMENTS

| 2,073,960 A | 3/1937 | Crosby |
| 2,140,593 A | 12/1938 | Pankonin |

(Continued)

FOREIGN PATENT DOCUMENTS

| EP | 0 251 444 A1 | 1/1988 |
| EP | 0 492 283 A1 | 7/1992 |

(Continued)

OTHER PUBLICATIONS

European Patent Office, Extended European Search Report for European Application No. EP 21173771.3, entitled "Reload Shaft Assembly for Surgical Stapler," dated Aug. 27, 2021, 10 pgs.
(Continued)

*Primary Examiner* — Dariush Seif
(74) *Attorney, Agent, or Firm* — John F. Heal

(57) ABSTRACT

A powered handle for a surgical stapler can have a drive system including an electric motor. The powered handle can include a manual return mechanism. The powered handle can also include a retention mechanism to prevent unintentional movement of drivetrain components upon actuation of the manual return mechanism. For example, the retention mechanism can apply a direction-dependent frictional force on an actuation shaft of the handle assembly to prevent unintentional movement of the actuation shaft towards a distal end of the handle assembly. The retention mechanism can include a featherboard-like configuration with a plurality of ribs oriented transversely to the actuation shaft to restrict movement of the actuation shaft in one direction while allowing movement of the shaft in the opposite direction.

17 Claims, 28 Drawing Sheets

(58) Field of Classification Search
USPC .......................................... 227/175.1–182.1
See application file for complete search history.

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,180,092 A | 1/1993 | Crainich |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,115 A | 11/1996 | Nicholas |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A * | 7/1998 | Mastri .................. A61B 17/072 227/175.3 |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |

(56) References Cited

U.S. PATENT DOCUMENTS

| | | |
|---|---|---|
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A * | 3/2000 | Mastri ............ A61B 17/07207 227/176.1 |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 * | 5/2006 | Mastri ............ A61B 17/07207 227/176.1 |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,364,061 B2 * | 4/2008 | Swayze ............ A61B 17/07207 227/176.1 |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |

(56) References Cited

U.S. PATENT DOCUMENTS

| | | |
|---|---|---|
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |

(56) References Cited

U.S. PATENT DOCUMENTS

| | | |
|---|---|---|
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0070958 A1* | 3/2005 | Swayze ............ A61B 17/07207 606/219 |
| 2005/0234478 A1 | 10/2005 | Wixey |
| 2006/0022015 A1* | 2/2006 | Shelton ............ A61B 17/07207 227/176.1 |
| 2006/0097026 A1 | 5/2006 | Shelton, IV |
| 2006/0100644 A1 | 5/2006 | Viola |
| 2006/0175375 A1* | 8/2006 | Shelton ............ A61B 17/07207 227/176.1 |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |

(56) References Cited

U.S. PATENT DOCUMENTS

| | | |
|---|---|---|
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0143806 A1 | 6/2009 | Witt et al. |
| 2009/0198272 A1 | 8/2009 | Kerver et al. |
| 2009/0206128 A1* | 8/2009 | Hueil .............. A61B 17/07207 227/176.1 |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Laurent et al. |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0109186 A1 | 5/2012 | Parrott et al. |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0253298 A1 | 10/2012 | Henderson et al. |
| 2012/0286022 A1 | 11/2012 | Olson et al. |
| 2012/0318844 A1* | 12/2012 | Shelton, IV ..... A61B 17/00234 227/176.1 |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0075448 A1* | 3/2013 | Schmid ............ A61B 17/07292 227/176.1 |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0146643 A1* | 6/2013 | Schmid ................ A61B 17/072 227/176.1 |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0032781 A1 | 12/2013 | Swayze et al. |
| 2013/0327809 A1 | 12/2013 | Shelton, IV et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |

(56) References Cited

U.S. PATENT DOCUMENTS

| | | |
|---|---|---|
| 2014/0203063 A1 | 7/2014 | Hessler et al. |
| 2014/0205637 A1 | 7/2014 | Widenhouse et al. |
| 2014/0224686 A1* | 8/2014 | Aronhalt ............ A61B 17/0644 |
| | | 206/339 |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1* | 9/2014 | Leimbach ............ A61B 17/064 |
| | | 227/176.1 |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1* | 9/2014 | Patel ................ A61B 17/07207 |
| | | 227/176.1 |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0007621 A1 | 3/2015 | Shelton, IV et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297219 A1* | 10/2015 | Shelton, IV ......... A61B 17/105 |
| | | 227/176.1 |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0100838 A1* | 4/2016 | Beaupré ............ A61B 17/07207 |
| | | 227/175.1 |
| 2016/0183948 A1 | 6/2016 | Shelton, IV et al. |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245824 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1* | 10/2017 | Reed .......................... H02J 7/00 |
| 2017/0290584 A1 | 10/2017 | Jasemian et al. |
| 2017/0319287 A1* | 11/2017 | Zergiebel ............ A61B 17/072 |
| 2018/0153545 A1* | 6/2018 | Zergiebel ............ A61B 17/072 |
| 2019/0261984 A1* | 8/2019 | Nelson ............ A61B 17/07207 |
| 2019/0290263 A1* | 9/2019 | Morgan .................. A61B 50/36 |
| 2019/0290265 A1* | 9/2019 | Shelton, IV .............. H02J 7/00 |
| 2020/0268381 A1 | 8/2020 | Roberts et al. |
| 2022/0133317 A1* | 5/2022 | Von Stein ........ A61B 17/07207 |
| | | 227/175.1 |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 044 893 A2 | 9/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |

(56) References Cited

FOREIGN PATENT DOCUMENTS

| RU | 2063710 | 7/1996 |
|---|---|---|
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |
| WO | WO 2020/077531 A1 | 4/2020 |

OTHER PUBLICATIONS

European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" dated Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" dated Feb. 11, 2022, 15 pgs.
European Patent Office, The International Search Report and the Written Opinion of the International Searching Authority for International Application No. PCT/US2021/057365, entitled "Surgical Stapler Having a Powered Handle" dated Apr. 13, 2022, 21 pgs.
European Patent Office, The International Search Report and the Written Opinion of the International Searching Authority for International Application No. PCT/US2022/012452, entitled "Surgical Stapler Having Shaft Recognition Mechanism" dated Apr. 13, 2022, 13 pgs.
European Patent Office, European Search Report for European Application No. 07784007.2, entitled "Surgical Stapler," dated Jun. 15, 2012, 6 pgs.
Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
European Patent Office, International Search Report and Written Opinion for International Application No. PCT/US2014/028211, entitled "Surgical Stapler with Partial Pockets," dated Sep. 8, 2014, 17 pgs.
International Searching Authority, U.S., The International Search Report and the Written Opinion of the International Searching authority for international application PCT/US2014/027768, titled "Surgical Stapler with Expandable Jaw", dated Jul. 25, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.

(56) References Cited

OTHER PUBLICATIONS

European Patent Office, Extended European Search Report for European Application No. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," dated Jul. 19, 2019, 24 pgs.

European Patent Office, Extended European Search Report for European Application No. EP 19150575.9, entitled "Surgical Stapler Having Actuation Mechanism with Rotatable Shaft," dated Aug. 21, 2019, 5 pgs.

European Patent Office, Extended European Search Report for European Application No. EP 19180055.6, entitled "Surgical Stapler with Circumferential Firing," dated Sep. 20, 2019, 8 pgs.

European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.

European Patent Office, Extended European Search Report for European Application No. EP 20157713.7, entitled "Surgical Stapler with Expandable Jaw," dated May 11, 2020, 6 pgs.

European Patent Office, Extended European Search Report for European Application No. EP 20161294.2, entitled "Surgical Stapler with Self-Adjusting Staple Height," dated Jun. 22, 2020, 6 pgs.

European Patent Office, Extended European Search Report for European Application No. EP 20197859.0, entitled "Surgical Stapler with Circumferential Firing," dated Jan. 28, 2021, 13 pgs.

International Searching Authority/ EPO, Invitation to Pay Additional Fees for PCTUS2020/025496, entitled "Reload Cover for Surgical Stapling System," dated Jun. 18, 2019, 15 pgs.

European Patent Office, The International Search Report and the Written Opinion of the International Searching Authority for International Application No. PCT/US2020/025496, entitled "Reload Cover for Surgical Stapling System," dated Aug. 13, 2020, 20 pgs.

The International Bureau of WIPO, International Preliminary Report on Patentability, for International Application No. PCT/US2019/019867, entitled "Surgical Stapler Having a Powered Handle," dated Sep. 3, 2020, 16 pgs.

European Patent Office, The International Search Report and Written Opinion for International Application No. PCT/US2020/067540, dated May 3, 2021, entitled "Electrosurgical System with Tissue and Maximum Current Identification," 12 pages.

The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.

The International Bureau of WIPO, International Preliminary Report on Patentability, for International Application No. PCT/US2020/025496 entitled "Reload Cover for Surgical System," dated Oct. 14, 2021, 12 pgs.

European Patent Office, Extended European Search Report for European Application No. EP 22196603.9, entitled "Surgical Stapler with Expandable Jaw," dated Dec. 14, 2022, 6 pgs.

European Patent Office, Extended European Search Report for European Application No. EP 22203464.7, entitled "Surgical Stapler with Partial Pockets," dated Dec. 20, 2022, 9 pgs.

European Patent Office, Extended European Search Report for European Application No. EP 22203599.0, entitled "Surgical Stapler Having a Powered Handle," dated Feb. 7, 2023, 7 pgs.

\* cited by examiner

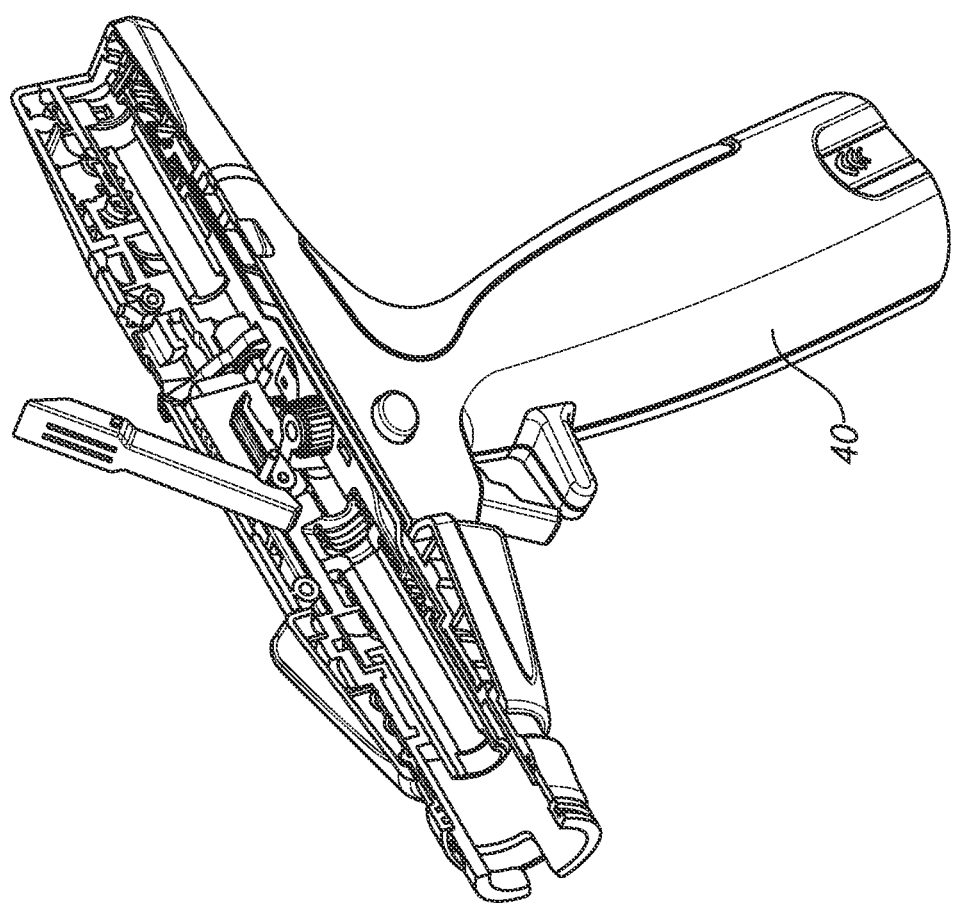
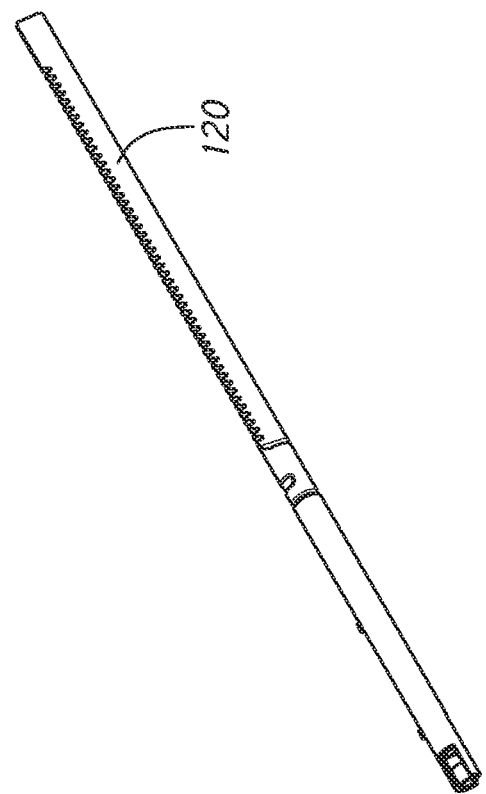
FIG. 13

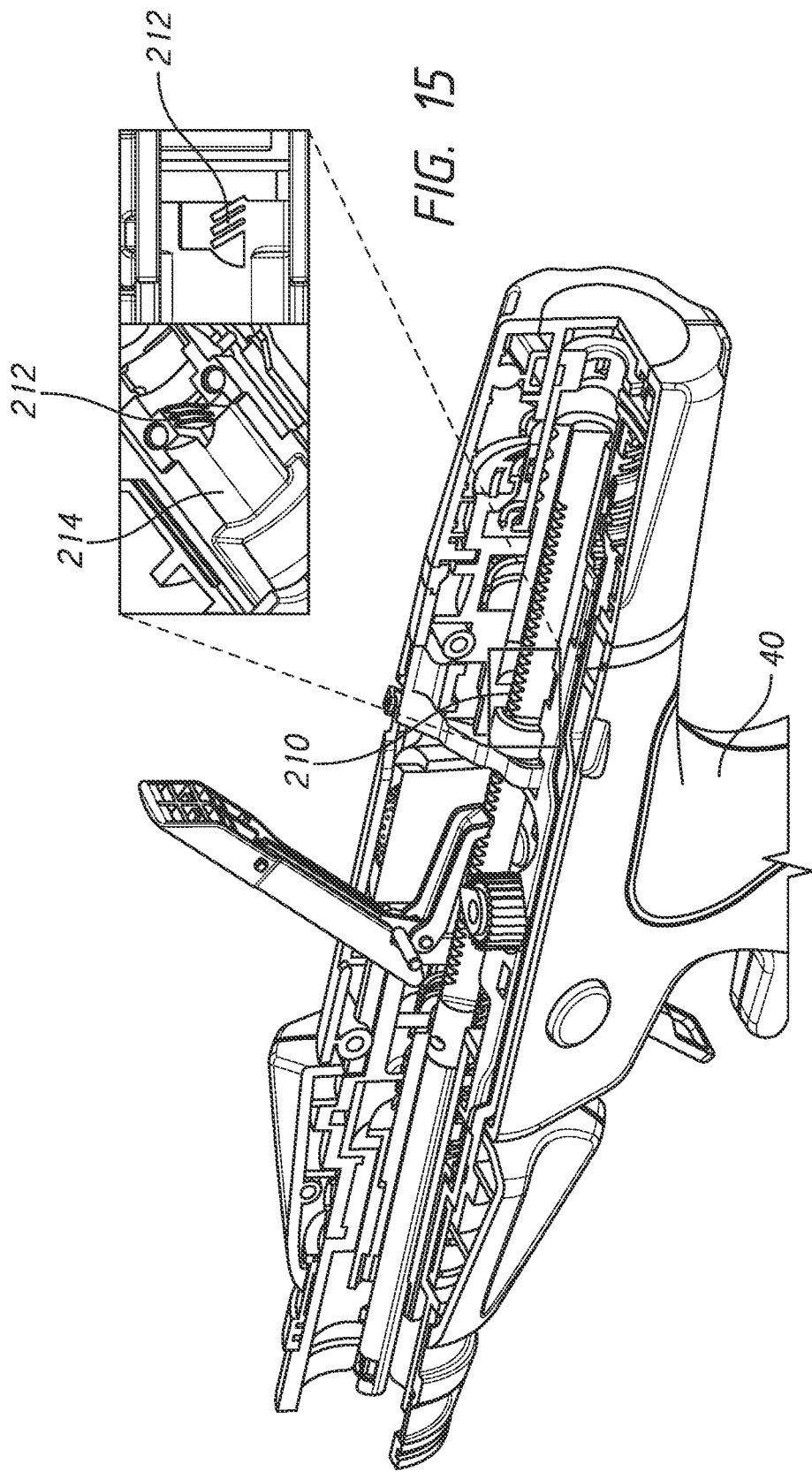

ACTUATION SHAFT RETENTION MECHANISM FOR SURGICAL STAPLER

CROSS-REFERENCE TO RELATED APPLICATIONS

This application claims priority to and benefit of U.S. Provisional Patent Application Ser. No. 63/107,112 entitled "Actuation Shaft Retention Mechanism for Surgical Stapler" filed on Oct. 29, 2020 which is incorporated herein by reference in its entirety.

BACKGROUND OF THE INVENTION

Field of the Invention

The present application relates generally to surgical occlusion instruments and, more particularly, to surgical staplers.

Description of the Related Art

Surgical staplers are used to approximate or clamp tissue and to staple the clamped tissue together. As such, surgical staplers have mechanisms to clamp tissue and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

Surgical staplers having electrically powered motors to clamp a jaw assembly and fire staples from the jaw assembly can facilitate stapling by reducing user effort for applying staples through tissue, reducing workload when multiple staple lines are placed during a procedure. It can be desirable that an electrically powered stapler has a manual return mechanism to allow a user to manually return the stapler to an initial configuration in certain instances.

SUMMARY OF THE INVENTION

In certain embodiments, a handle assembly for a surgical stapler is provided. The handle assembly comprises a handle body, an electric motor, an actuation shaft, a mechanical return mechanism, and a retention mechanism. The handle body comprises a stationary handle and a trigger pivotably coupled to the handle body. The electric motor is disposed within the handle body. The actuation shaft is slidable within the handle body along a longitudinal axis and rotatable within the handle body about the longitudinal axis. The actuation shaft comprises a rack formed thereon. The retention mechanism is configured to restrict distal longitudinal advancement of the actuation shaft upon actuation of the mechanical return mechanism.

In certain embodiments, a handle assembly for a surgical stapler is provided. The handle assembly comprises a handle body, an electric motor, an actuation shaft, a mechanical return mechanism, and a plurality of fins engageable with the actuation shaft. The handle body comprises a stationary handle and a trigger pivotably coupled to the handle body. The electric motor is disposed within the handle body. The actuation shaft is slidable within the handle body along a longitudinal axis and rotatable within the handle body about the longitudinal axis. The actuation shaft comprises a rack formed thereon. The plurality of fins is engageable with the actuation shaft upon actuation of the mechanical return mechanism. The plurality of fins extends transversely to the longitudinal axis to allow movement of the actuation shaft in a proximal direction and restrain the actuation shaft from movement in a distal direction.

In certain embodiments, a handle assembly for a surgical stapler is provided. The handle assembly comprises a handle body, an electric motor, an actuation shaft, a mechanical return mechanism, and a retention mechanism. The handle body comprises a stationary handle and a trigger pivotably coupled to the handle body. The electric motor is disposed within the handle body. The actuation shaft is slidable within the handle body along a longitudinal axis and rotatable within the handle body about the longitudinal axis. The actuation shaft comprises a rack formed thereon. The mechanical return mechanism comprises a shaft rotation mechanism and a shaft retraction mechanism. The retention mechanism is configured to prevent distal longitudinal advancement of the actuation shaft upon actuation of the shaft retraction mechanism. The actuation shaft is rotatable from a first position wherein the rack is operationally engaged with the electric motor to longitudinally slide the actuation shaft to a second position wherein the rack is disengaged from the electric motor and engaged with the manual return mechanism and engaged with the retention mechanism.

BRIEF DESCRIPTION OF THE DRAWINGS

FIG. 13 is a partial cut-away perspective view of the powered handle of FIG. 2 with an actuation shaft removed from an actuation mechanism;

FIG. 14 is a partial cut-away perspective view of the powered handle of FIG. 2 with an embodiment of actuation shaft retention mechanism;

FIG. 15 is a detail view of the actuation mechanism of FIG. 14;

DETAILED DESCRIPTION OF THE INVENTION

Figure 1:
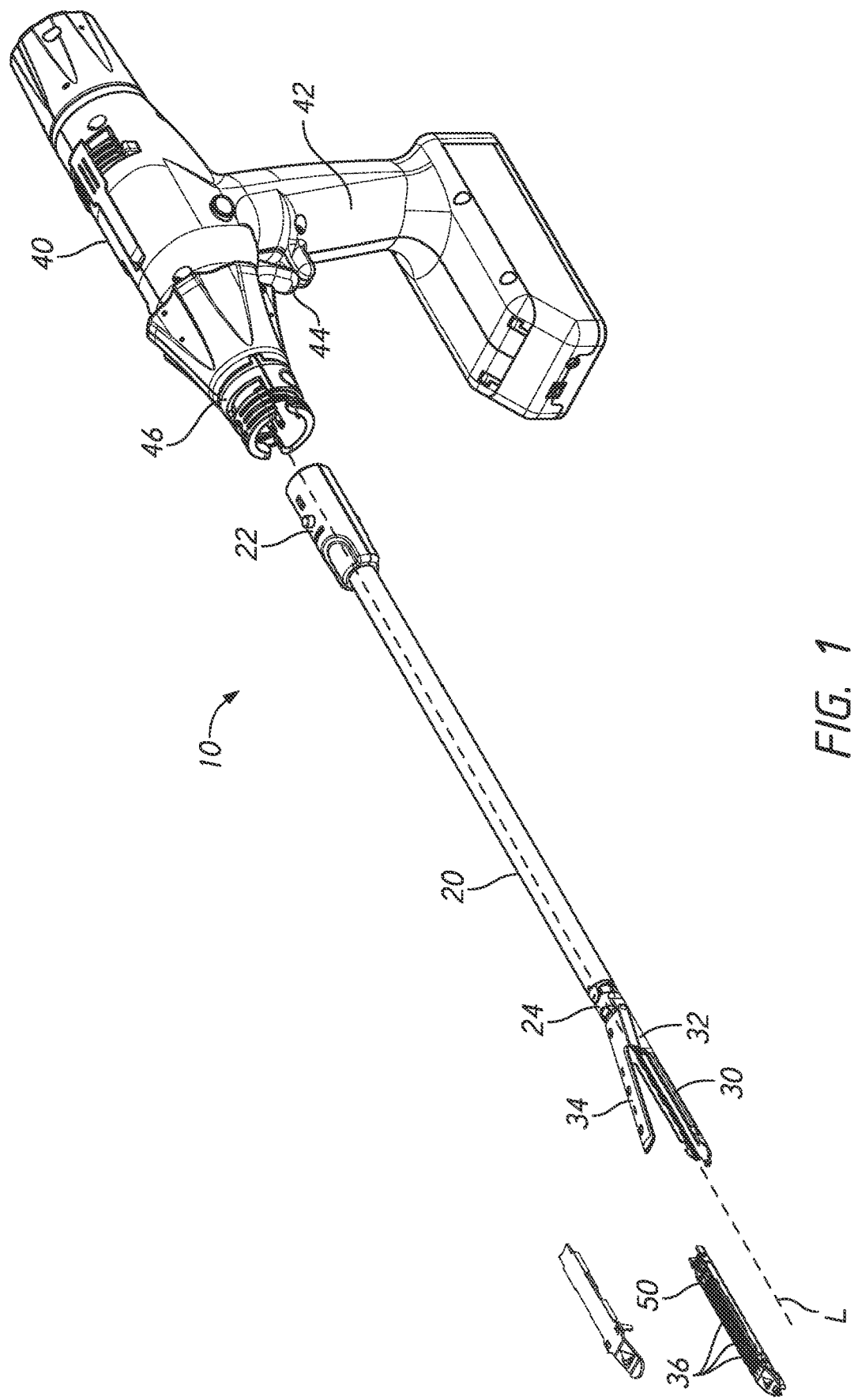
FIG. 1 is a perspective view of an embodiment of surgical stapling system having an embodiment of powered handle.
Figure 2:
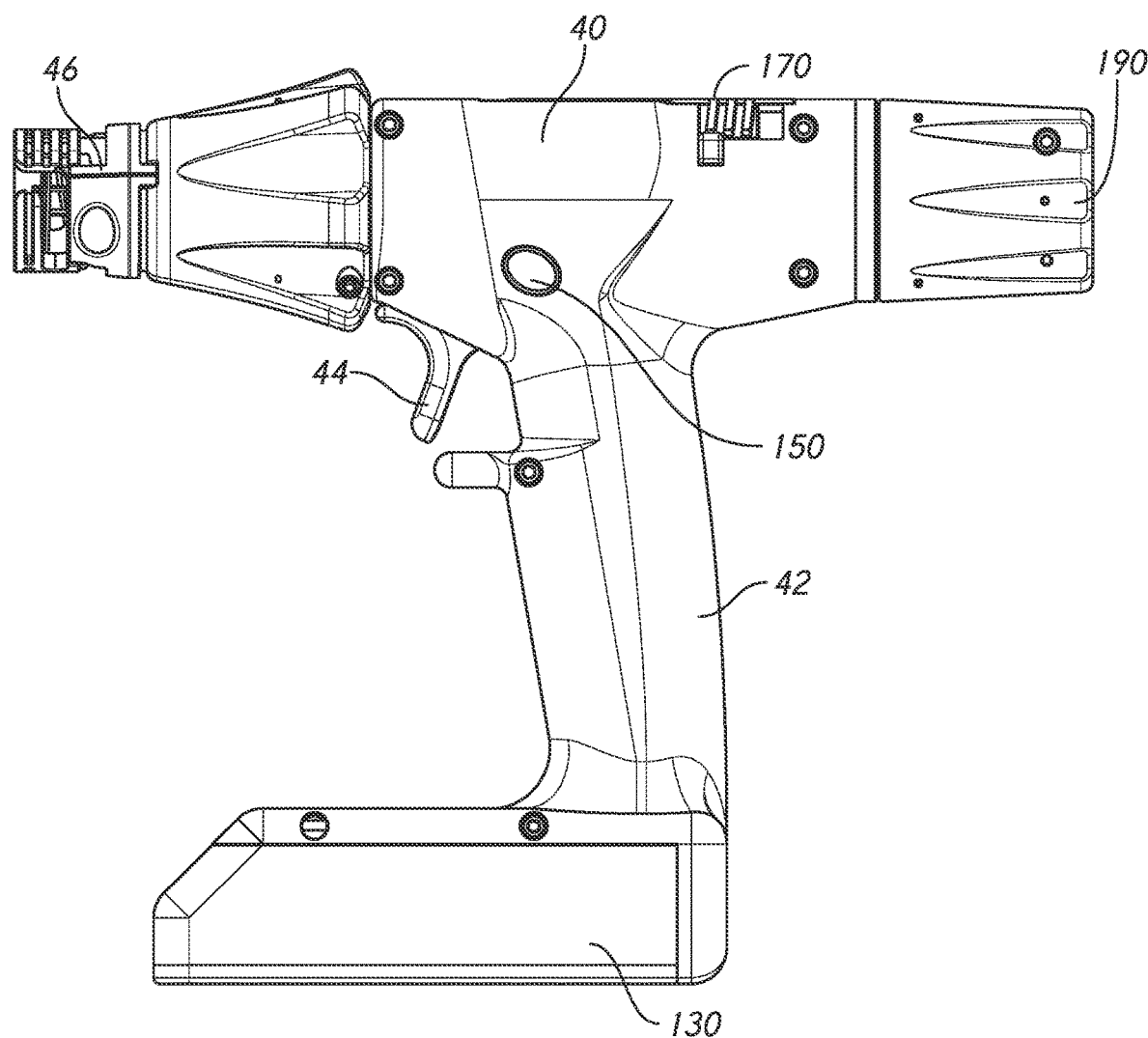
FIG. 2 is a side view of the powered handle of the surgical stapling system of FIG. 1.

With reference to FIGS. 1-2, an embodiment of surgical stapling system is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration with an embodiment of powered handle having powered staple firing and manual jaw assembly articulation. FIG. 2 illustrates the powered handle 40 of the surgical stapler system 10 with the elongate shaft removed. The powered handle 40 of FIG. 2 has powered staple firing and manual jaw assembly articulation. In the illustrated embodiments, the shaft 20 and jaw assembly 30 can be freely rotated about a longitudinal axis defined by the shaft 20 by rotation of a rotation knob on the handle 40. In other embodiments, the stapling system can be configured to allow rotation of the jaw assembly about the longitudinal axis within a predefined range or a rotationally fixed jaw assembly.

With continued reference to FIG. 1, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIG. 1, as illustrated, the elongate shaft 20 comprises a generally tubular member. The elongate shaft 20 extends from a proximal end to a distal end. The elongate shaft 20 defines a central longitudinal axis, L. of the surgical stapler 10 extending between the proximal end 22 and the distal end 24.

With continued reference to FIG. 1, in the illustrated embodiment, the jaw assembly 30 is coupled to the elongate shaft 20 at the distal end of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and is articulable with respect to the elongate shaft 20 responsive to an articulation mechanism in the handle 40. In an initial configuration, the first jaw 32 includes a plurality of staples 36 disposed therein within a reload 50. In other embodiments, the reload 50 can be integrated with the jaw assembly 30 such that the entire shaft assembly 20 and jaw assembly 30 with loaded staples define a single reload assembly. In some embodiments, staples can be initially positioned in the second jaw 34.

With continued reference to FIG. 1, in the illustrated embodiment, the jaw assembly 30 can be actuated from an open configuration (FIG. 1) to a closed configuration to a stapling configuration by a drive member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the reload 50 in the first jaw 32.

With continued reference to FIG. 1, in the illustrated embodiment, the handle assembly is configured to be coupled to the elongate shaft 20 at the proximal end of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. As further described in greater detail below, the handle assembly 40 houses a powered actuation mechanism configured to selectively advance an actuation shaft responsive to movement of the movable handle 44.

In the illustrated embodiment, the surgical stapler 10 can include the plurality of staples 36 positioned in a disposable cartridge reload 50 while the jaw assembly 30 is configured to be reused with multiple staple cartridge reloads 50 in a single procedure. In the some embodiments, the elongate shaft 20 and jaw assembly 30 define a disposable reload shaft that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10. The coupler 46 can have a bayonet connection having an outer connector that can removably couple the handle assembly 42 to the elongate shaft 20, a first inner connector that can removably couple the actuation shaft of the handle assembly 42 to the drive member of the elongate shaft 20, and a second inner connector that can removably couple an articulation coupler of the handle assembly 42 to an articulation link of the elongate shaft 20. These three removable couplings occur simultaneously when an elongate shaft 20 is coupled to the handle assembly 42. Accordingly, the surgical stapler 10 can be configured such that the handle assembly 40 can be reused with multiple reload shafts 20 during a surgical procedure. It is contemplated that in other embodiments, the handle assembly and some portion of the elongate shaft can be reusable while a remainder of the elongate shaft in the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

With reference to FIG. 2, an embodiment of powered handle for a surgical stapling system is illustrated. The powered handle can be used with various shaft reloads and cartridges such that the shaft configuration, jaw assembly configuration, and staple configuration can be selected for a particular procedure. The illustrated embodiment of handle provides powered (motor-driven) clamping and closing of the jaws and firing of the staple line. Articulation of the jaw assembly can be manually controlled by an articulation knob that the operator rotates. The motor is controlled by an embedded control system that dictates functionality of the handle during different stages of use.

With continued reference to FIG. 2, the powered handle 40 comprises a pistol-grip configuration with a stationary handle 42 and a movable handle 44 or trigger pivotably coupled thereto. A power supply 130 or battery can be positioned on a lower surface of the stationary handle. The powered handle 40 can further comprise a user control such as a fire or fire/reverse button 150 to allow a user to selectively control a stapling sequence. The powered handle 40 can further comprise a redundant, manual override return system 170 to allow a user to manually return the stapling system to an open configuration in the event of a powered system failure, control system failure, power supply failure, "lockjaw," or other mechanical binding. The powered handle can further comprise a manual articulation mechanism including a rotatable articulation knob 190. In the illustrated embodiment, the articulation knob 190 is positioned on the proximal end of the powered handle and is rotatable about an axis generally corresponding to the longitudinal axis of the stapling system. In some embodiments, the powered handle can further include an illuminated user display, such as an annular light ring to display desired status indicia to a user.

Various embodiments of powered handle assemblies and associated actuation mechanisms are disclosed in U.S. patent application Ser. No. 15/486,227, filed Apr. 12, 2017, entitled "Reload Shaft Assembly for Surgical Stapler" and U.S. patent application Ser. No. 15/486,008, filed Apr. 12, 2017, entitled "Surgical Stapler Having a Powered Handle," both of which are incorporated by reference herein in their entireties.

Powered Drive System

Figure 3:
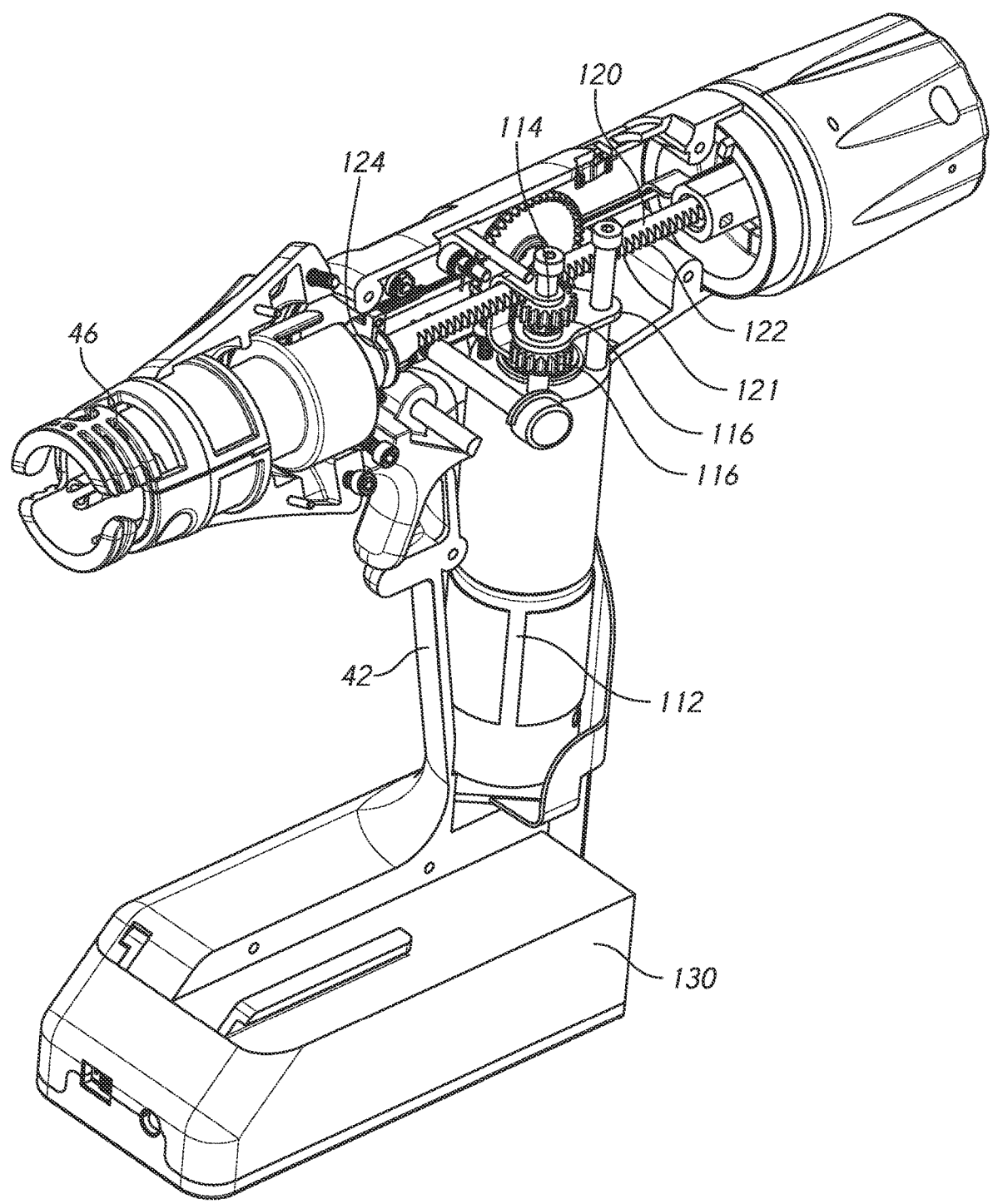
FIG. 3 is a partial cutaway perspective view of the powered handle of FIG. 2 with components removed to illustrate a drive system thereof.

With reference to FIG. 3, a partial cut-away view of the powered handle is illustrated. In the illustrated cut-away view, several components of the powered handle have been removed to clearly depict a drive system of the powered handle. In the illustrated embodiment, the drive system comprises a motor 112 positioned within the stationary handle 42, a motor gear 114 positioned on an output shaft of the motor 112, and an auxiliary gear 116 in driven engagement with the motor gear 114. In some embodiments, the motor 112 is a brushed DC gearmotor. Advantageously, transmitting power through the auxiliary gear 116 can allow the motor 112 to be laterally centered within the stationary handle to enhance handle balance and user ergonomics. Furthermore, in some embodiments, the motor gear 114 and auxiliary gear 116 can be configured to provide a desired operational torque at the rack 122. In some embodiments, the motor 112 can include a multigear transmission operationally coupled between the motor 112 and the motor gear 114 coupled to the auxiliary gear 116 to provide the desired operational torque. The motor 112 can be electrically coupled to the power supply 130 via a control system. The control system within the handle interfaces with the drive system to measure the position of the actuation shaft 120 and therefore the actuation of the jaw assembly.

The drive system is mounted to hardware that provides information to a control system including a microcontroller within the handle. This embedded system can control the speed and torque of the motor. It can also control functionality of the device based on user inputs (movement of the trigger and pressing of the FIRE/REVERSE button) and position of the drive system. The control system can also measure feedback from the motor to determine whether loads are too high to continue firing staples, or whether a reload cartridge lockout has been activated. It can also measure battery life and can limit the number of firings of the device. While the drive system is configured primarily for powered operation, in certain embodiments it can be desirable to provide a manual return mechanism to override powered operation as further described herein.

With continued reference to FIG. 3, in the illustrated embodiment, the drive system comprises a bifurcated auxiliary gear 116 that is supported between its endpoints by a support plate 121. Advantageously, this supported arrangement for the auxiliary gear 116 provides a robust mechanism that can significantly reduce a tendency of the motor gear 114 from separating from the auxiliary gear 116 in heavy loading conditions. In other embodiments, the drive system can comprise an auxiliary gear that is not bifurcated.

Manual Override Return System

With reference to FIGS. 4-12C an embodiment of manual return mechanism for the powered handle is illustrated. A manual return mechanism can advantageously provide a redundant return mechanism in the event of a power supply failure, other powered component failure, or mechanical failure or binding.

Figure 4:
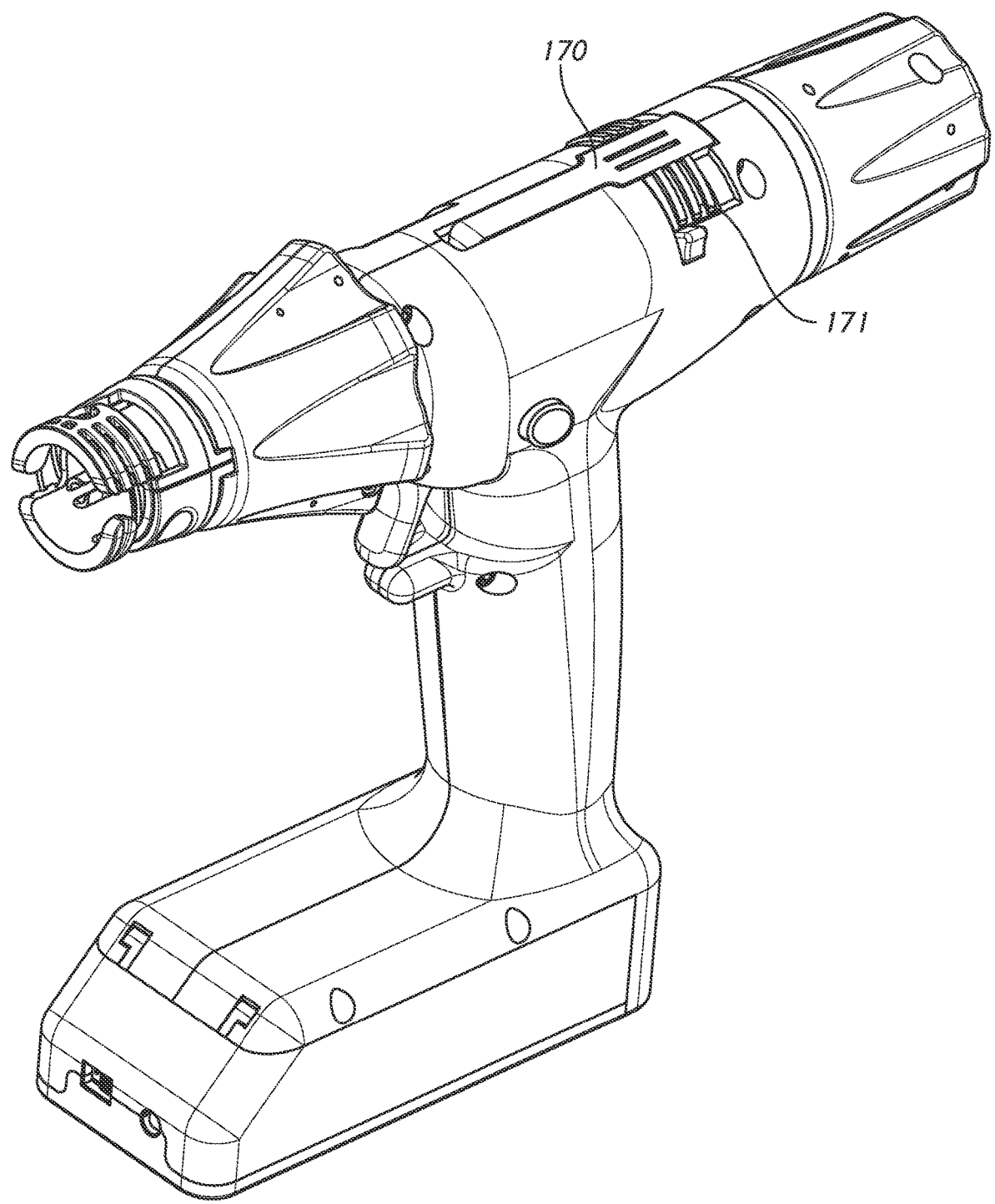
FIG. 4 is a perspective view of the powered handle of FIG. 2 with an override return mechanism in a disengaged configuration.

With reference to FIGS. 4-11, the manual return mechanism includes three separate, independently operable subassemblies that are operated in sequence to return the actuation shaft 120 to a proximal-most position within the handle, which corresponds to the open configuration of the jaw assembly. As illustrated, the manual return mechanism 170 comprises a return lock mechanism, a shaft rotation mechanism, and a shaft retraction mechanism. FIG. 4 illustrates the powered handle in a powered operation mode, with the return lock mechanism in a locked configuration. In operation, when it is desirable to manually return the stapler to the open configuration, the return lock mechanism is initially actuated to unlock the manual return mechanism.

Figure 5:
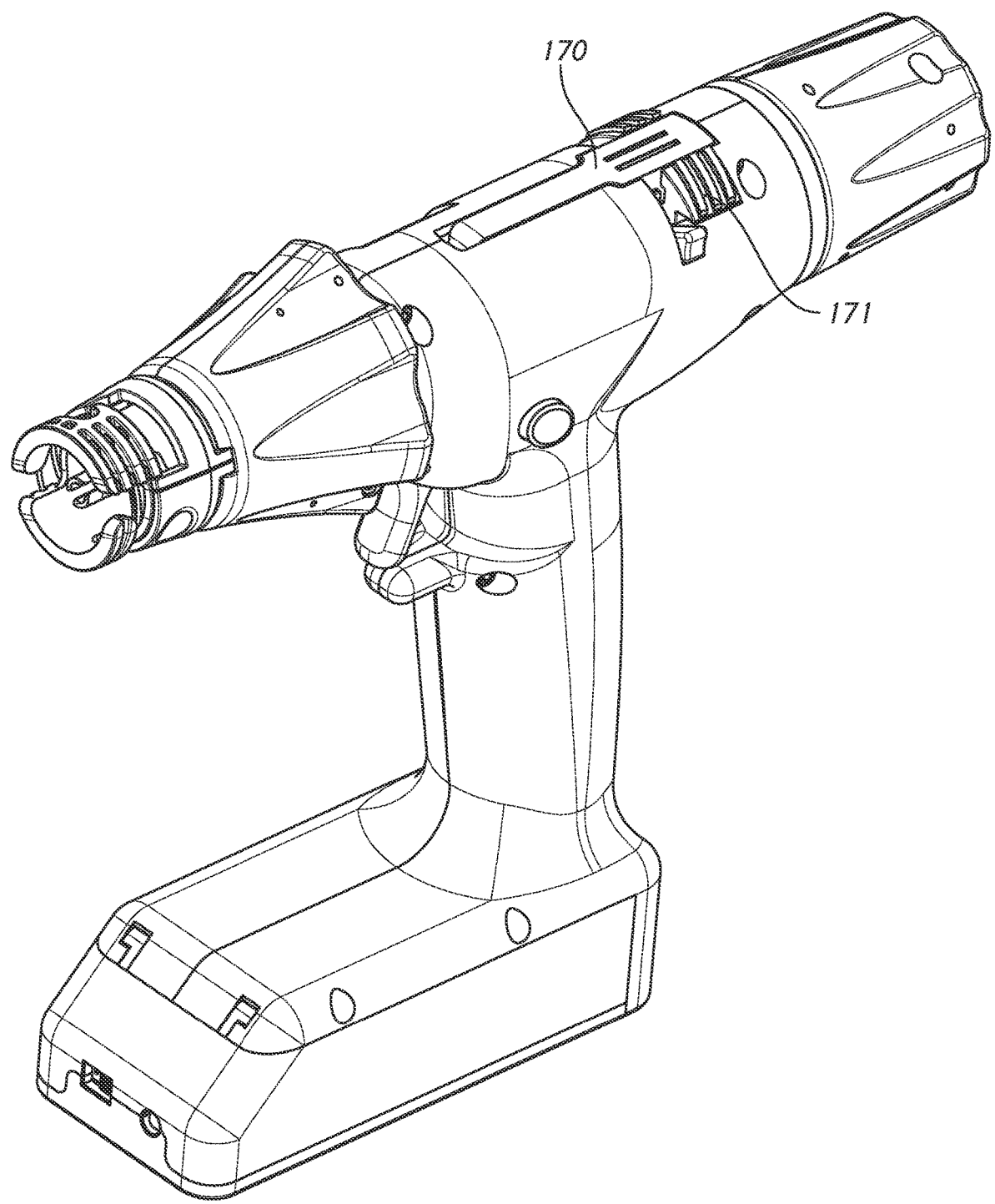
FIG. 5 is a perspective view of the powered handle of FIG. 2 with the override return mechanism unlocked for movement to a return configuration.
Figure 6:
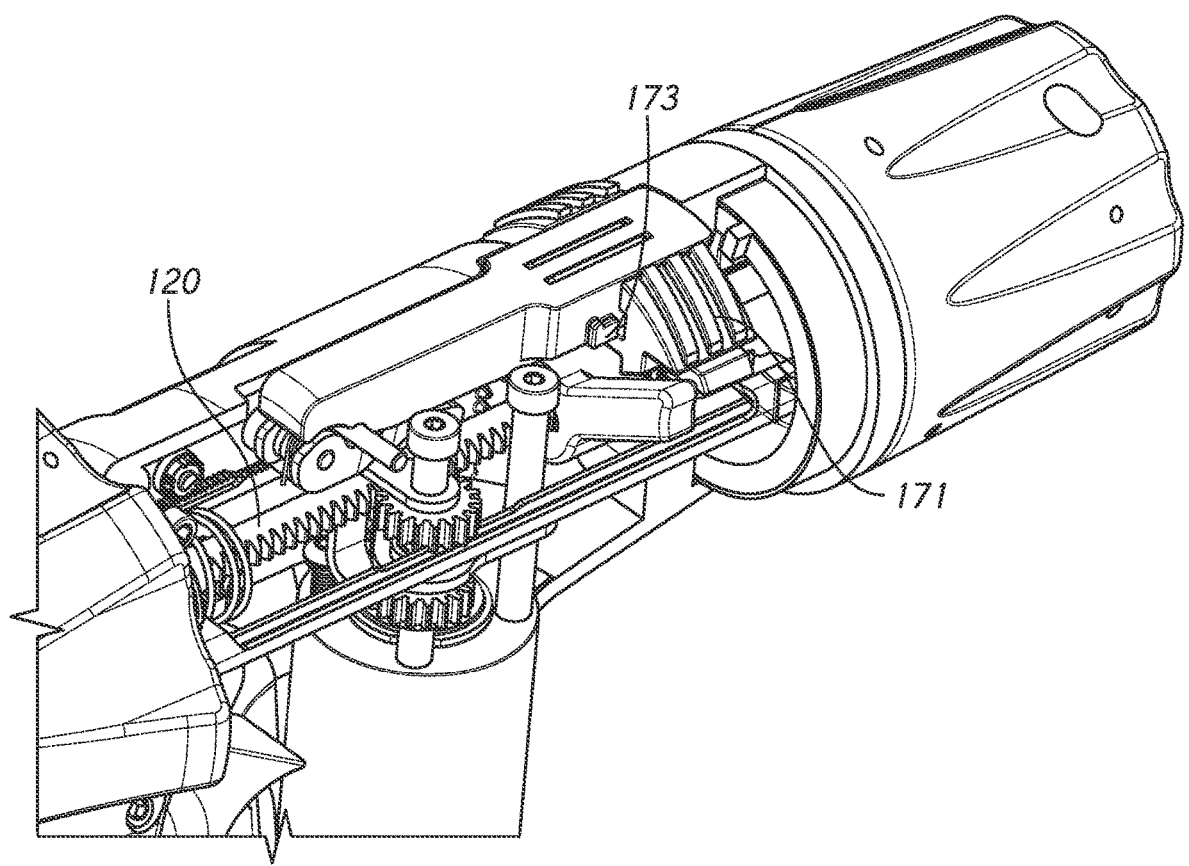
FIG. 6 is a perspective partial cut-away view of the powered handle of FIG. 2 with the override return mechanism unlocked for movement to a return configuration.

As illustrated in FIGS. 5-6, to actuate the return lock mechanism, a return lock 171 is initially slid proximally with respect to the housing of the handle assembly. This movement of the return lock 171 unlocks the shaft rotation mechanism and the shaft retraction mechanism. In the illustrated embodiment, the return lock 171 is moved off of a position in which it interfered with movement of the shaft rotation mechanism, exposing the shaft rotation mechanism for use. Simultaneously, the return lock 171 is disengaged from lock protrusions 173 or tabs on the shaft retraction mechanism allowing the shaft retraction mechanism to pivot away from the handle assembly. A lever of the shaft retraction mechanism can be biased away from the handle assembly, causing it to pivot away from the handle assembly when the return lock is slid proximally.

Figure 7:
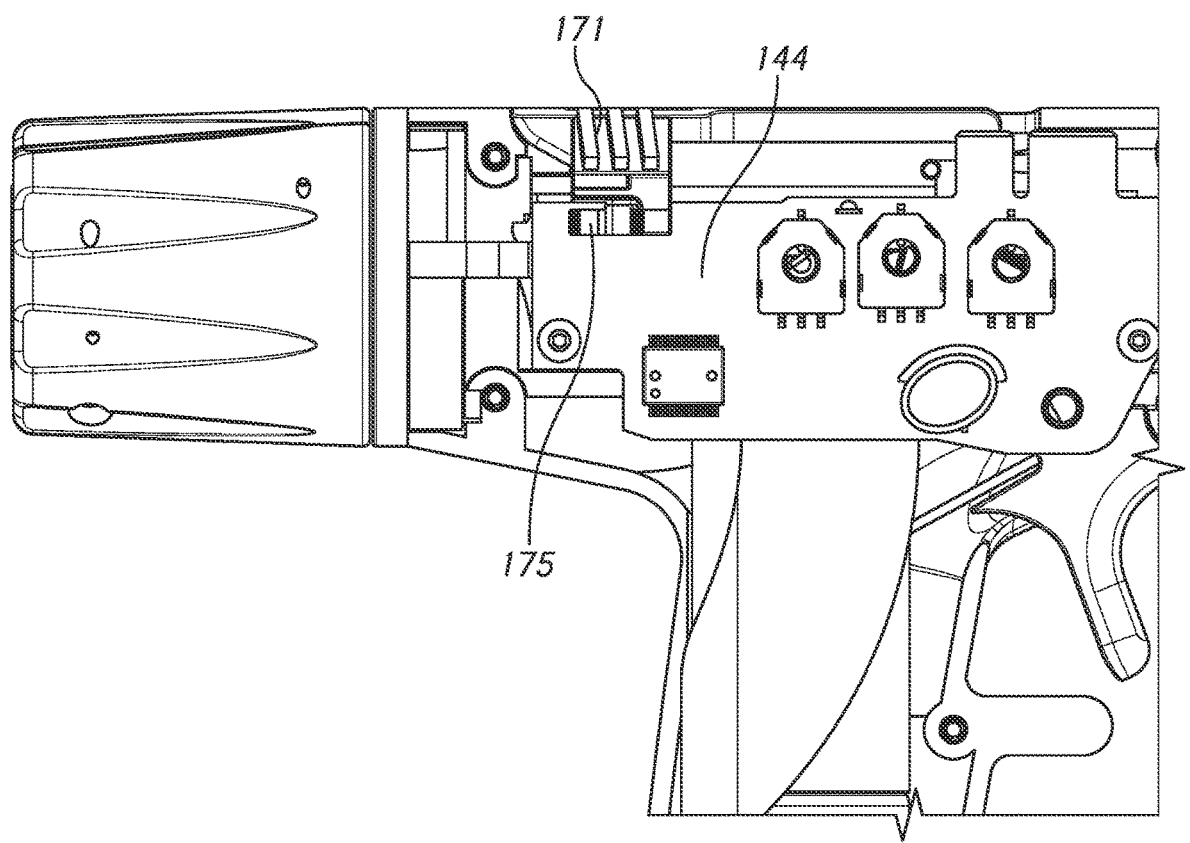
FIG. 7 is a partial cut-away side view of the powered handle of FIG. 2 with the override return mechanism in a disengaged configuration.
Figure 8:
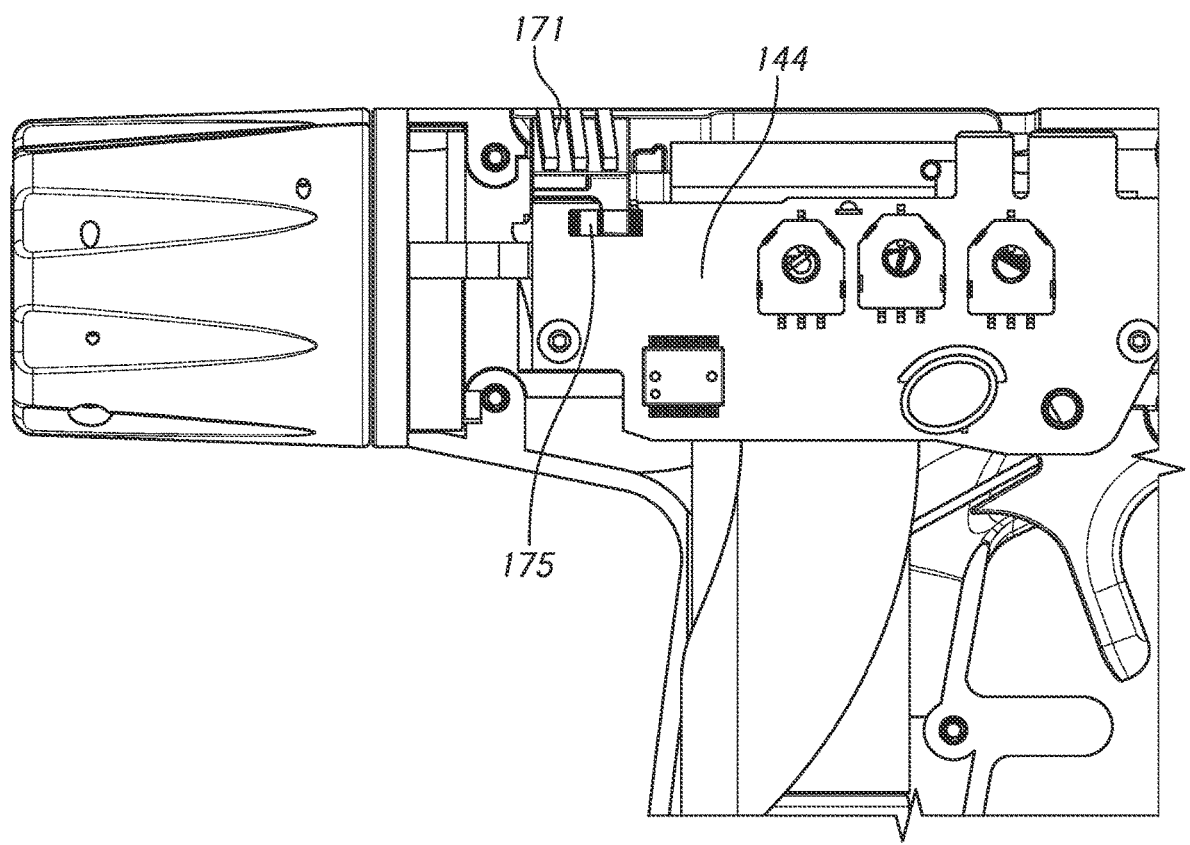
FIG. 8 is a partial cut-away side view of the powered handle of FIG. 2 with the override return mechanism unlocked for movement to a return configuration.

With reference to FIGS. 7 and 8, when the return lock is slid proximally to unlock the return mechanism, the return lock 171 can be electrically coupled to the control unit of the handle assembly to depower the handle assembly. Thus, once the return lock mechanism has been operated, the handle can be disabled from further use even if a user attempts to manually reposition the manual return mechanism and the drive system for repeat use. In the illustrated embodiment, when the handle assembly is configured for powered operation (FIG. 7), the return lock is electrically disengaged from the circuit board 144 having the control unit. In certain embodiments, when the return lock is slid proximally to unlock the return mechanism, the return lock proximally moves a stamped spring component 175 that electrically engages a circuit on the circuit board 144 to depower the handle assembly. The spring component 175 is configured for proximal movement only and does not return distally even if the return lock is returned distally to its initial position. Thus, unlocking the return mechanism by sliding the return lock 171 permanently disables the powered functionality of the handle assembly.

Figure 9:
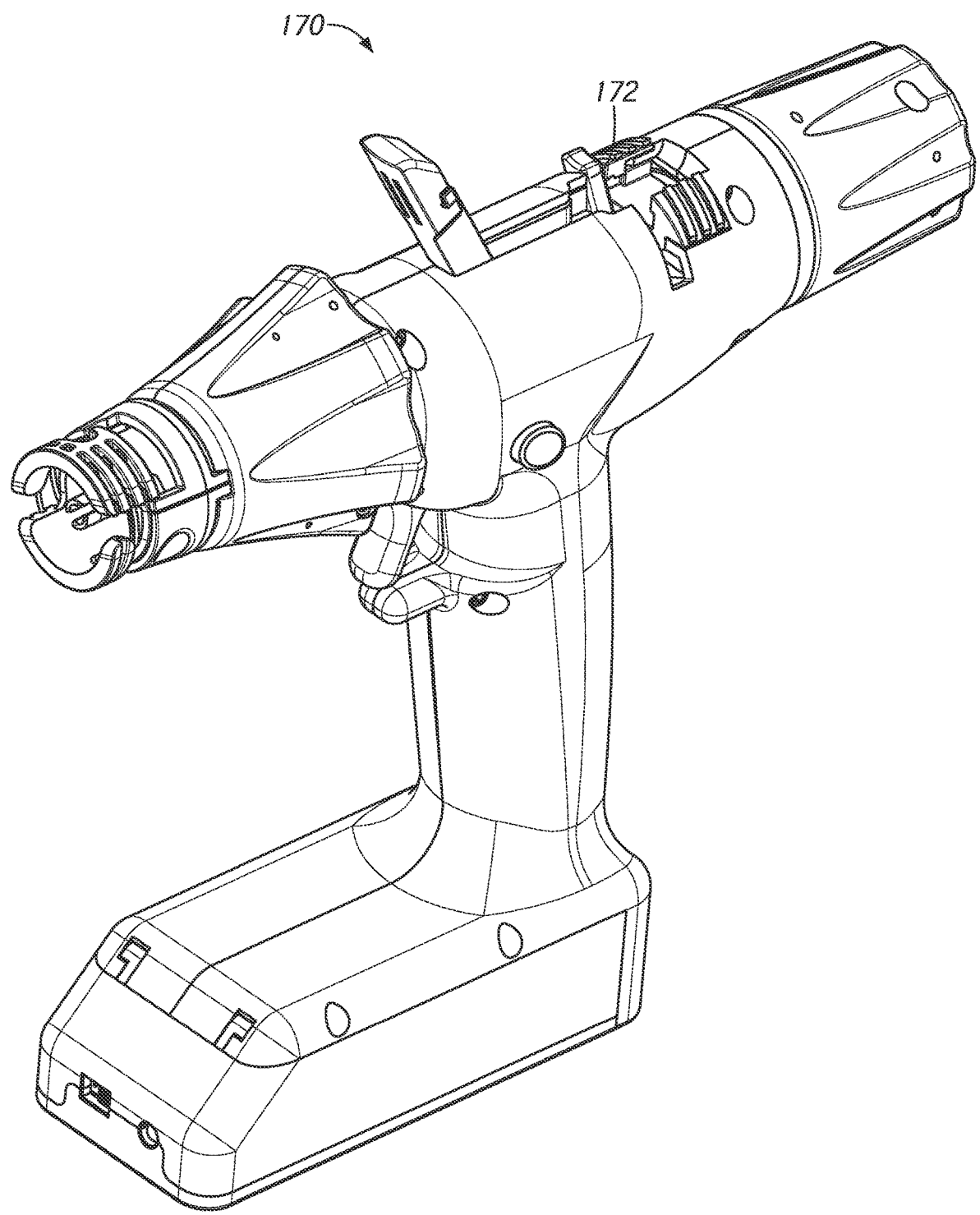
FIG. 9 is a perspective view of the powered handle of FIG. 2 with the override return mechanism in a return configuration.
Figure 10:
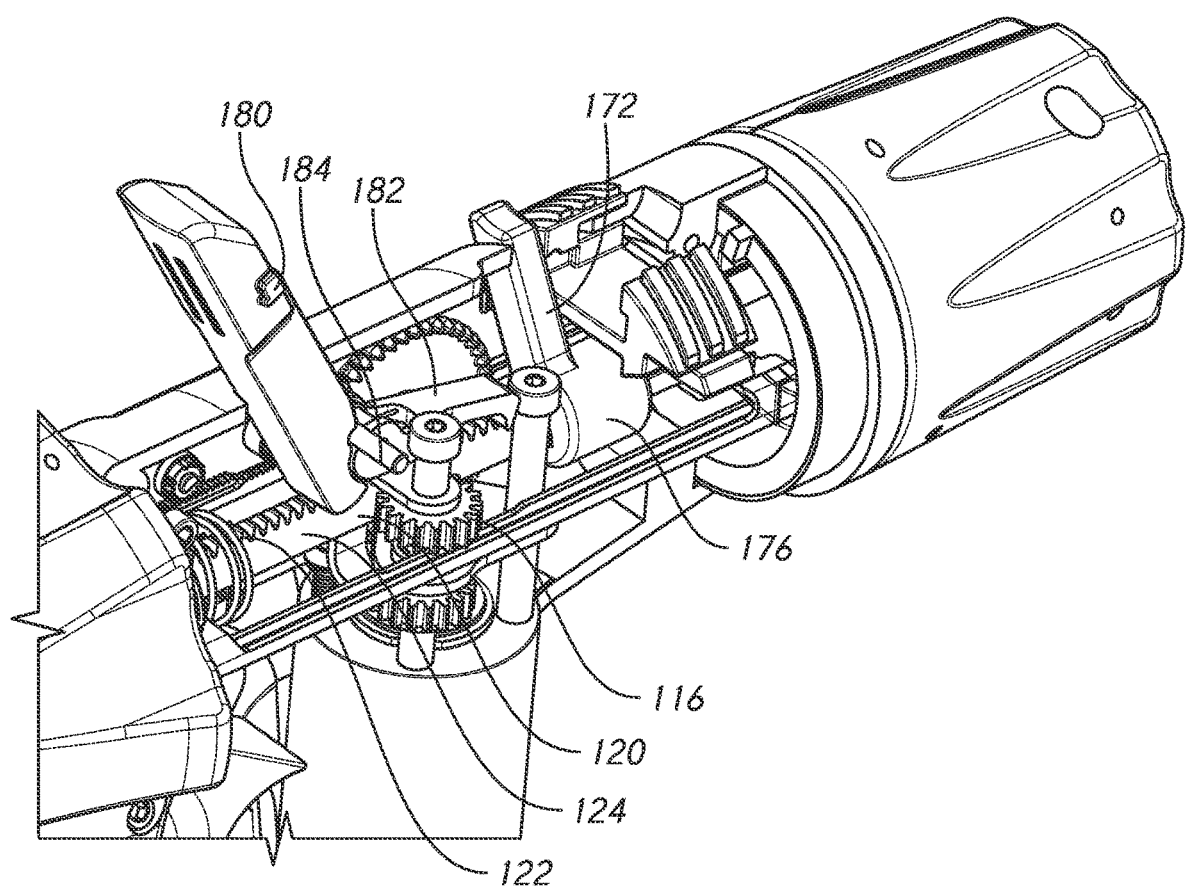
FIG. 10 is a perspective partial cut-away view of the powered handle of FIG. 2 with the override return mechanism in a return configuration.

With reference to FIGS. 9 and 10, to operate the shaft rotation mechanism of the manual return mechanism 170, a user rotates a rotation lever 172 extending to on an outer surface of the handle, now unblocked by movement of the return lock. The rotation lever 172 is coupled to a shaft rotation collar rotationally coupled to the actuation shaft. In the illustrated embodiment, the actuation shaft 120 extends through the shaft rotation collar 176 and is slideable therethrough. Thus, rotating the shaft rotation collar 176 rotates the actuation shaft 120 approximately 90 degrees about the longitudinal axis thereof. This rotation positions the rack 122 of the actuation shaft out of engagement with the auxiliary gear 116 of the drive system. This rotation can be accomplished without affecting the actuation adapter since the actuation shaft 120 is rotatably coupled to the actuation adapter (FIG. 3). In certain embodiments, the actuation shaft comprises a recessed outer surface 124 extending adjacent the rack 122 such that when the actuation shaft 120 is rotated to disengage the rack 122 from the auxiliary gear 116, the recessed outer surface 124 is spaced apart from the auxiliary gear 116.

While the illustrated embodiment includes a shaft rotation mechanism having a rotation lever 172 rotated by a user, in other embodiments, the shaft rotation mechanism can be configured to self-deploy upon proximal movement of the return lock. For example, a self-deploying shaft rotation mechanism can include a shaft rotation collar having a torsional bias. In certain embodiments, the shaft rotation collar is coupled to the handle assembly by a torsion spring. When the return lock is slid proximally, the torsional bias of the shaft rotation tends to rotate the actuation rack to disengage the actuation rack from the auxiliary gear and to engage the actuation rack with the shaft retraction mechanism.

Figure 11:
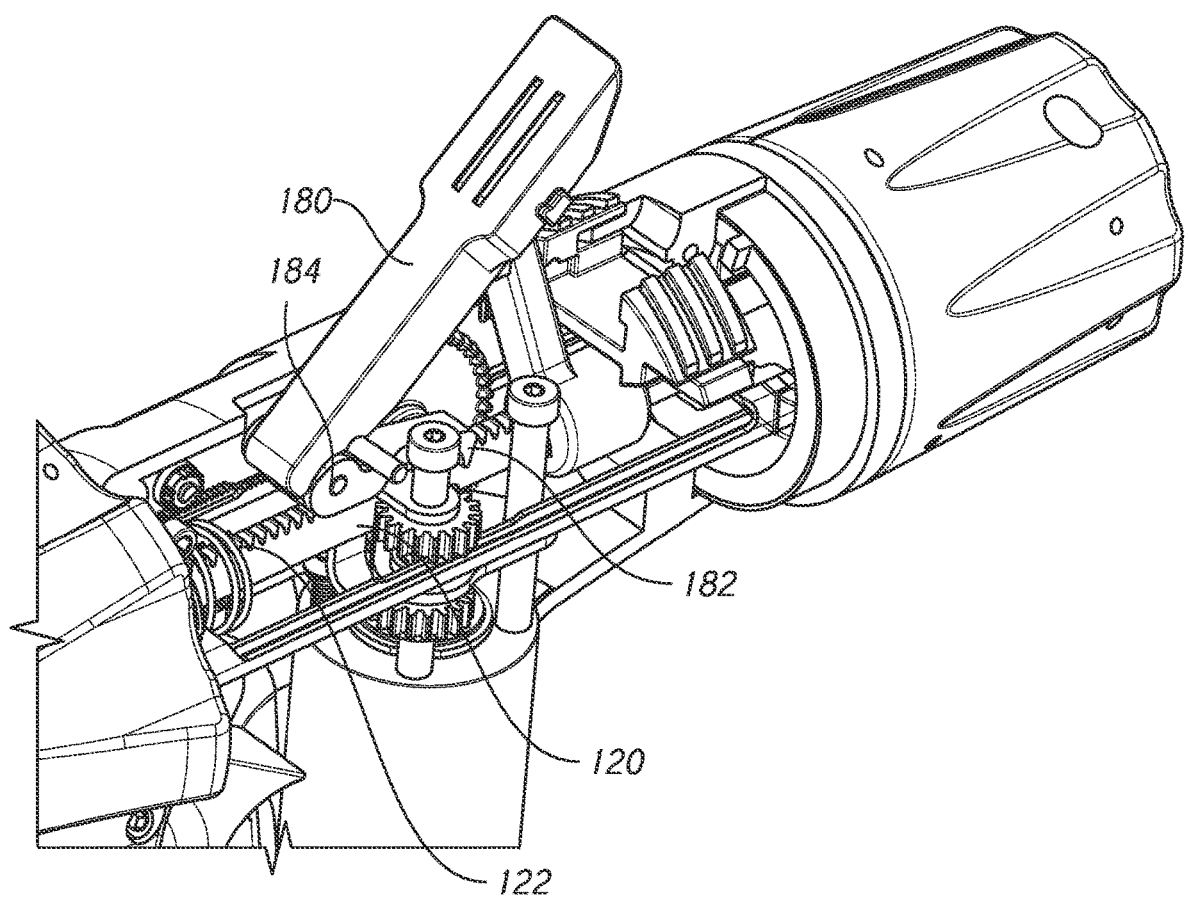
FIG. 11 is a perspective partial cut-away view of the powered handle of FIG. 2 with the override return mechanism in a return configuration and a manual return cycle initiated.

With reference to FIGS. 10 and 11, once the shaft rotation mechanism has been operated, the shaft retraction mechanism can be operated to return the actuation shaft proximally within the handle. Sliding the return lock proximally within the handle assembly unlocks a return lever 180 on the powered handle. The return lever 180 is pivotably coupled to a return pawl 182 at a pivot joint 184. When the rack 122 of the actuation shaft 120 was rotated out of engagement with the drive system, it was rotated into engagement with the shaft retraction mechanism. The return lever 180 can be rotated through one or a series of return cycles (FIGS. 10, 11) to engage the return pawl 182 with the rack 122 on the actuation shaft 120 and retract the actuation shaft 120 proximally within the handle in a ratchet-type operation.

Figure 12A:
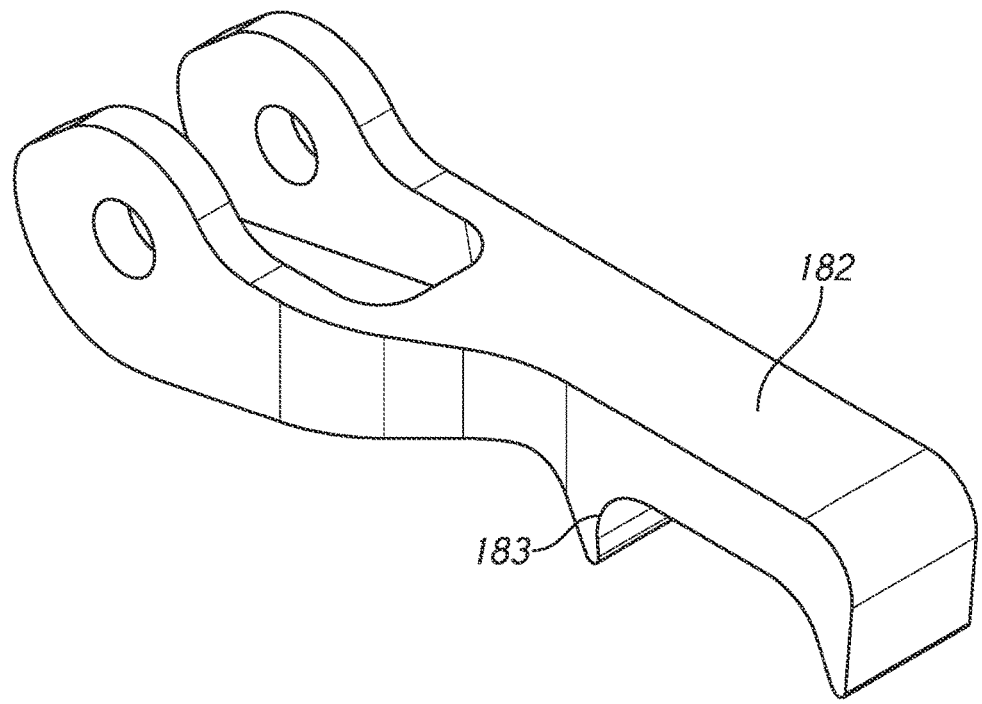
FIG. 12A is a perspective view of a return pawl of the override return mechanism of the powered handle of FIG. 2.
Figure 12B:
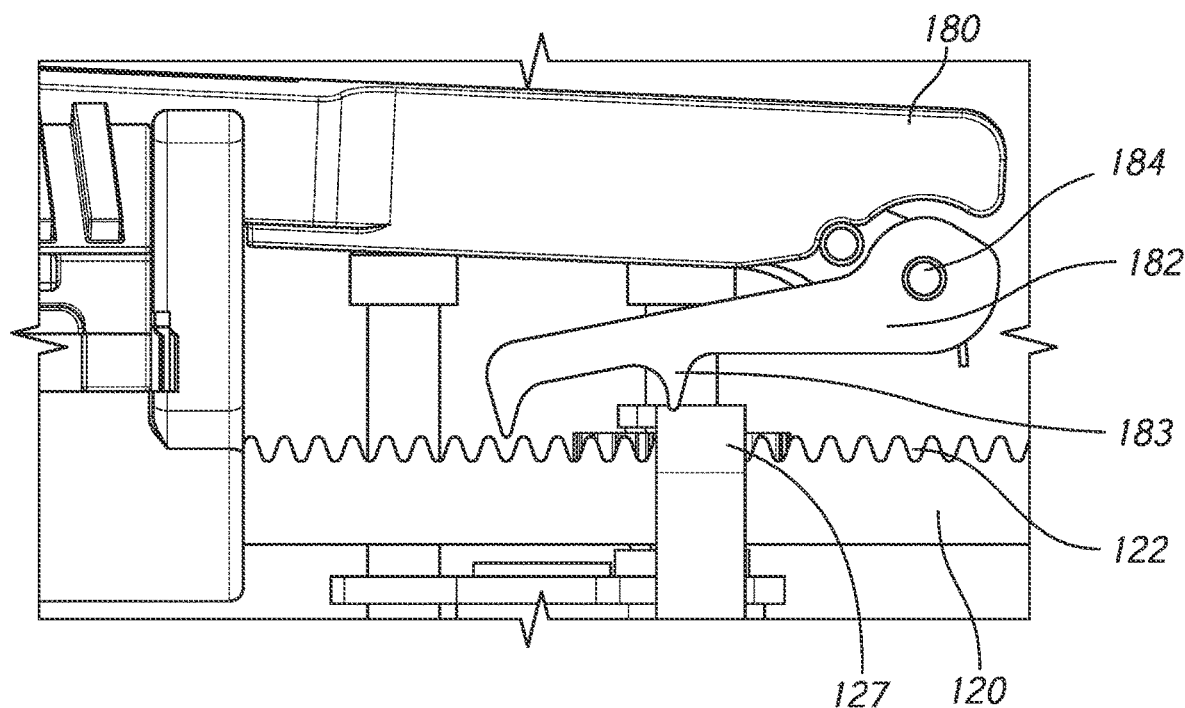
FIG. 12B is a side view of the override return mechanism of the powered handle of FIG. 2.
Figure 12C:
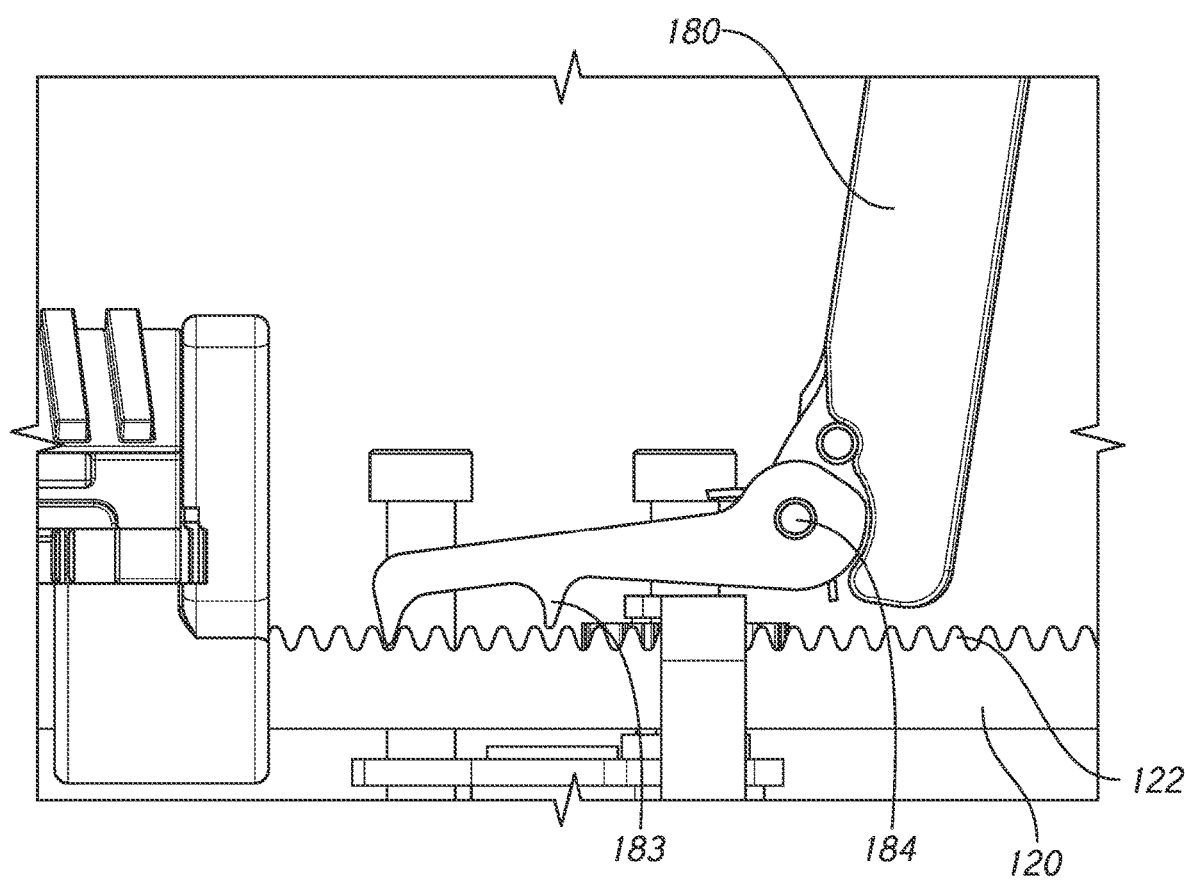
FIG. 12C is a side view of the override return mechanism of the powered handle of FIG. 2.

With reference to FIGS. 12A-12C, the return pawl 182 can be configured to facilitate actuation shaft retraction. In the illustrated embodiment, the return pawl 182 comprises a protruding boss or second pawl tooth 183 that is positioned to interact with the guide member 127 of the motor mount during a portion of the return cycle. During powered operation, the second pawl tooth 183 contacts the guide member 127, and the return pawl 182 is limited from engaging the rack 122 of the actuation shaft 120 (FIG. 12B). Desirably, the second pawl tooth 183 can be positioned to limit engagement of the return pawl 182 with the rack 122 during a portion of the return cycle where a user would otherwise have relatively low mechanical advantage. As illustrated, the second pawl tooth 183 prevents the return pawl 182 from engaging the rack 122 until the return lever 180 is positioned at a predetermined angle relative to a longitudinal axis of the actuation shaft 120 to provide a desired mechanical advantage (FIG. 12C).

With reference to FIG. 13, a partial cut away perspective view of a handle assembly 40 for a surgical stapler is illustrated. In powered operation, an actuation shaft 120 of a handle assembly remains operably coupled to a drive system to clamp jaws of an end effector and fire staples over one or more firing cycles. Should the manual return mechanism be actuated to disengage the actuation shaft from the drive system and return the actuation shaft to a proximal position, in certain instances, following operation of the manual return mechanism and removal of the elongate shaft from the handle assembly 40, the actuation shaft 120 can become disengaged from both the drive system and the manual return mechanism. In these circumstances, the actuation shaft can migrate distally and partially or fully out of the handle assembly. For example, if the handle assembly 40 were oriented with a distal end pointed downward, in certain instances, the weight of the actuation shaft 120 can cause it to move distally relative to the handle assembly. FIG. 13 illustrates a handle assembly in a condition with an actuation shaft moved distally fully out of the handle assembly. While such a condition, occurring only following actuation of the manual return mechanism and decoupling of the elongate shaft, would not pose a risk to a patient, it is desirable to maintain the integrity of the handle assembly following actuation of the manual return mechanism. However, in certain embodiments it is desirable that the handle assembly 40 further comprises a retention mechanism to prevent or reduce the likelihood of distal movement of the actuation shaft 120 following operation of the manual return mechanism.

Actuation Shaft Retention Mechanism

With reference to FIGS. 14-19, certain aspects of an embodiment of retention mechanism 210 for a manual return mechanism are illustrated. In the illustrated embodiment, the retention mechanism 210 comprises a featherboard-like plurality of fins 212 or ribs positioned to allow movement of the actuation shaft in a proximal direction when engaged by the manual return mechanism and restrict movement of the actuation shaft in a distal direction.

With reference to FIGS. 14-15, in certain embodiments, a plurality of fins 212 can be disposed in a handle assembly 40 housing adjacent the actuation shaft 120. As illustrated, in some embodiments, a featherboard geometry comprising a plurality of fins 212 can be integrally formed with a support housing 214 for the actuation shaft 120 within the handle assembly 40. For example, in certain embodiments, the support housing 214 can be formed by an injection molding process and the plurality of fins 212 can be injection molded with the support housing 214.

With continued reference to FIGS. 14-15, in the illustrated embodiment, the featherboard geometry comprises a plurality of fins 212 or ribs that are arranged at an angle transverse to a longitudinal axis of the actuation shaft 120. This transverse arrangement of the plurality of fins 212 can desirably impart a directionally dependent frictional force to the actuation shaft 120. With the plurality of fins 212 in contact with the actuation shaft 120, the plurality of fins 212 impart a first frictional force to the actuation shaft 212 when the actuation shaft is moved in a proximal direction relative to the handle assembly and a second frictional force, greater than the first frictional force, when the actuation shaft is moved in a distal direction relative to the handle assembly. Thus, desirably, the transverse angle configuration of the plurality of fins 212 can have a relatively small impact in additional frictional forces on an input force applied to the manual return mechanism to return the actuation shaft proximally within the handle assembly. But, the actuation shaft is restrained from moving distally within the handle assembly by the second frictional force.

Figure 16:
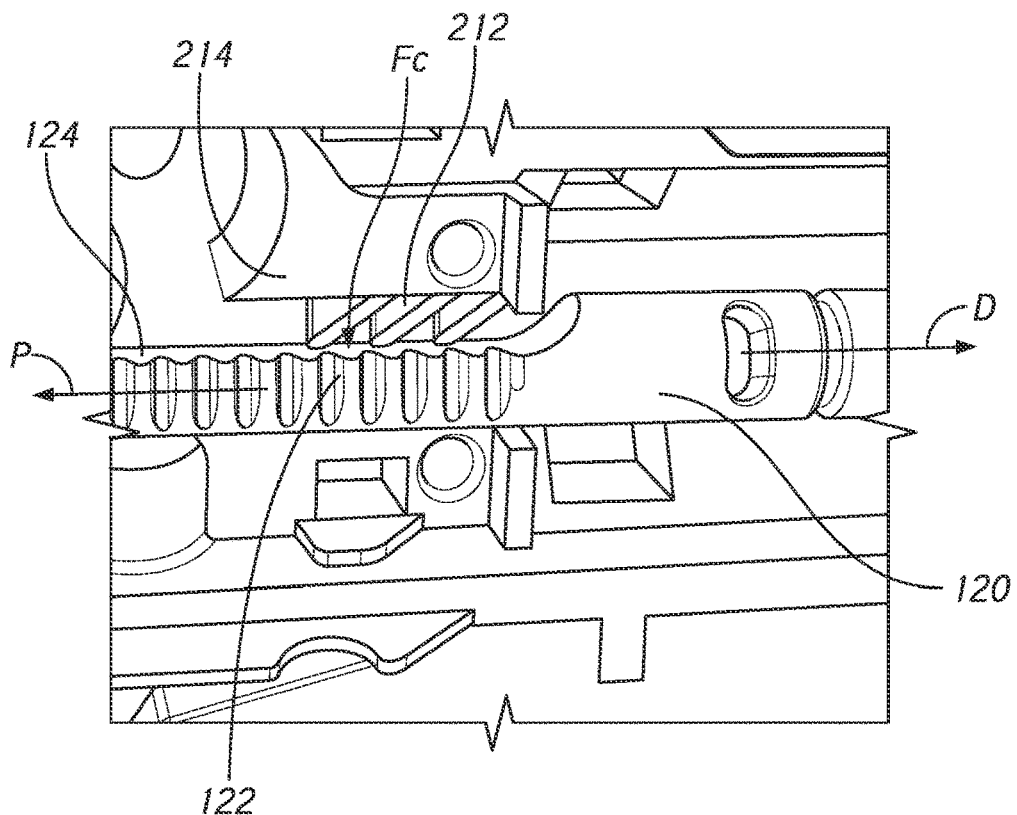
FIG. 16 is a detail view of the retention mechanism of FIG. 14.

With reference to FIG. 16, an embodiment of actuation shaft 120 disposed in an embodiment of support housing 214 for a handle assembly is illustrated. In the embodiment of FIG. 16, only the actuation shaft 120 and support housing 214 are illustrated and other components of a handle assembly are hidden to enhance visualization of certain aspects the interaction of the actuation shaft with the support housing. In the illustrated embodiment, the actuation shaft 120 is rotated to a return orientation for proximal return relative to the handle assembly with the manual return mechanism. The actuation shaft 120 is also illustrated in a fully proximally retracted position, corresponding to a full actuation of the manual return mechanism. As illustrated, the support housing 214 comprises a retention mechanism having a featherboard geometry. comprising a plurality of ribs or fins 212 formed in a surface of the support housing 214 and positioned to contact the actuation shaft 120. As illustrated, the plurality of ribs extends at an angle transverse to a longitudinal axis of the actuation shaft. 120 and apply a contact force Fc to the actuation shaft 120. Thus, the plurality of ribs imparts a directionally dependent frictional force on the actuation shaft. When the actuation shaft is moved in a proximal direction P relative to the support housing, such as when the manual return mechanism is actuated, the retention mechanism imparts a first frictional force to the actuation shaft. When the actuation shaft is moved in a distal direction D relative to the support housing, the retention mechanism imparts a second frictional force greater than the first frictional force to the actuation shaft.

Figure 17:
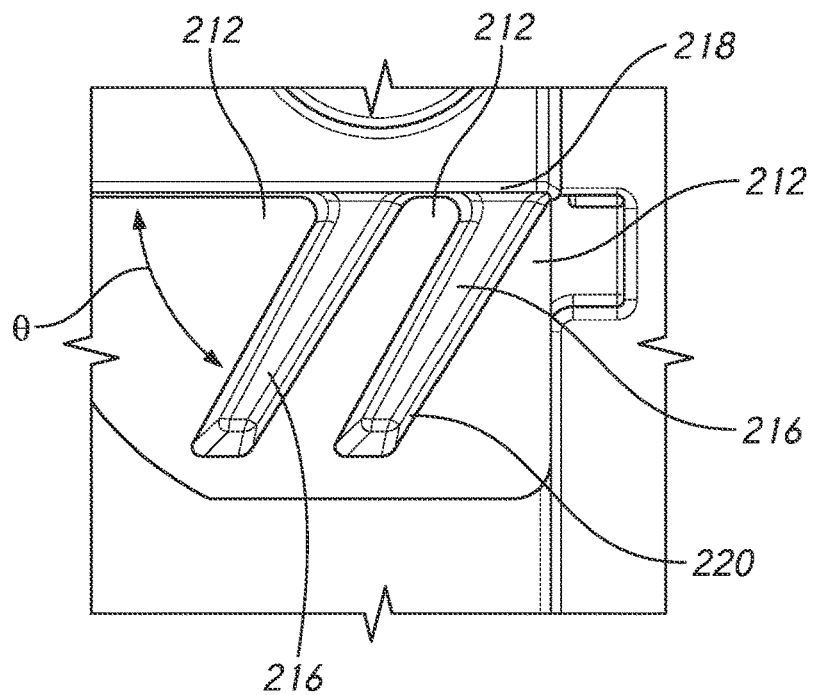
FIG. 17 is a detail view of the retention mechanism of FIG. 14.

With reference to FIG. 17, a detail view of embodiment of featherboard geometry for a handle assembly is illustrated. As illustrated, the featherboard geometry comprises a plurality of fins 212 or ribs. Adjacent ribs of the plurality of ribs are separated by a gap 216. Each gap comprises an open end 218 adjacent a tip of one of the plurality of ribs and a closed end 220 adjacent a root of one of the plurality of ribs. In some embodiments, the gap completely separates a pair of adjacent ribs. In other embodiments, the gap can separate a portion of a pair of adjacent ribs and the ribs can be joined over another portion. For example, the ribs can extend a height from the support housing.

With continued reference to FIG. 17, in certain embodiments the open end is longitudinally displaced relative to the longitudinal axis of the actuation shaft from the corresponding closed end such that each rib extends along an axis at an angle θ transverse to a longitudinal axis of the actuation shaft. In certain embodiments, the rib can extend at an angle relative to the longitudinal axis of the actuation shaft between approximately 30 degrees and 75 degrees. More desirably, the rib can extend at an angle between approximately 45 degrees and 70 degrees. Preferably, the rib can extend at an angle between approximately 55 degrees and 65 degrees. In other embodiments, the rib can extend at an angle less than 30 degrees or greater than 75 degrees relative to the longitudinal axis of the actuation shaft. In the illustrated embodiment, the featherboard geometry comprises two gaps 216 that are parallel to one another. It is contemplated that in other embodiments each gap can extend at a different angle relative to the longitudinal axis of the actuation shaft.

With continued reference to FIG. 17, in the illustrated embodiment, the featherboard geometry comprises two gaps 216 defining ribs therebetween. In other embodiments, a featherboard geometry for use in a retention mechanism can comprise more than two gaps defining ribs therebetween. Moreover, while the featherboard geometry in the illustrated embodiment is molded into a support housing component of the handle assembly, it is contemplated that in other embodiments, a featherboard component can be formed separately and bonded or fastened to a support housing.

Figures 18, 19:
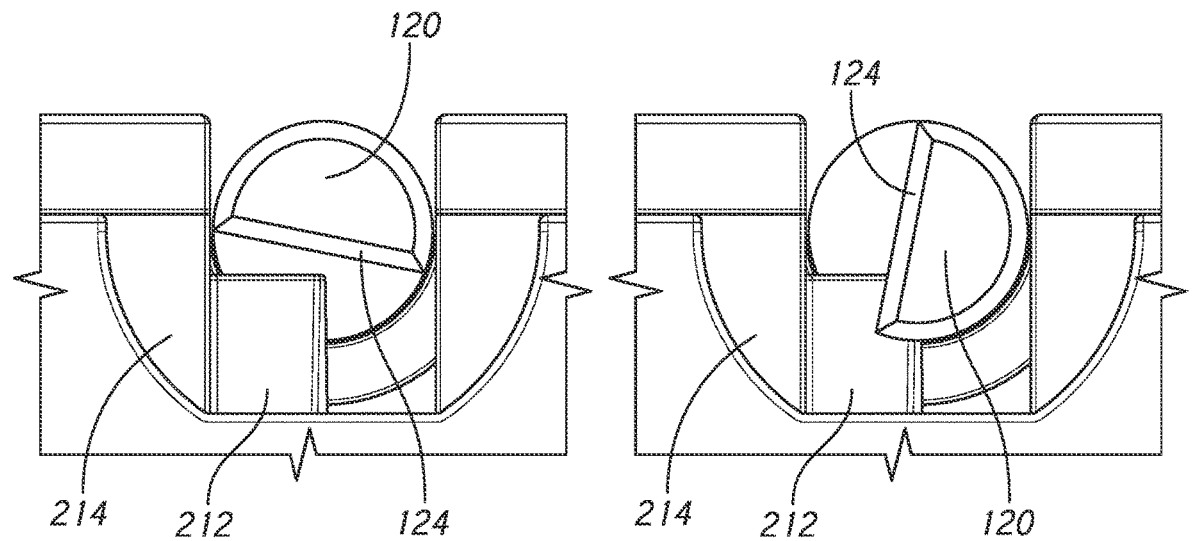
FIG. 18 is a cross sectional end view of the actuation shaft and retention mechanism of FIG. 14 with the override return mechanism in a disengaged configuration.
FIG. 19 is a cross sectional end view of the actuation shaft and retention mechanism of FIG. 14 with the override return mechanism in a return configuration.

With reference to FIGS. 18-19, an embodiment of actuation shaft 120 disposed in an embodiment of support housing 214 for a handle assembly is illustrated. FIGS. 18 and 19 illustrate a cut away end view of the actuation shaft 120 in the support housing 214 with the actuation shaft 120 oriented for powered actuation (FIG. 18) as compared with the actuation shaft 120 oriented for actuation of the manual return mechanism (FIG. 19). It is desirable that the retention mechanism is arranged such that it does not interfere with powered operation of the handle assembly but does retain the actuation shaft from distal migration once the manual return mechanism has been actuated. In certain embodiments, the featherboard geometry can be disposed within the handle assembly at a location spaced apart from the actuation shaft 120 when the actuation shaft is oriented for powered operation of the handle assembly and engaged with the actuation shaft when the actuation shaft has been rotated to an orientation for operation of the manual return mechanism.

With reference to FIG. 18, with the actuation shaft oriented for powered operation of the handle assembly, in certain embodiments the ribs of the retention mechanism are positioned within the support housing 214 at a location aligned with the recessed outer surface 124 of the actuation shaft 120. Thus, the retention mechanism is out of engagement with the actuation shaft 120 when the actuation shaft is oriented for powered operation of the handle assembly, allowing proximal and distal travel of the actuation shaft responsive to the drive system.

With reference to FIG. 19, with the actuation shaft 120 oriented for retraction of the actuation shaft with the manual return mechanism, the ribs of the retention mechanism are positioned within the support housing 214 at a location engaging a portion of the outer surface of the actuation shaft 120. Accordingly, with the actuation shaft 120 oriented for actuation with the manual return mechanism, the retention mechanism imparts a friction force to the actuation shaft 120.

Figure 20:
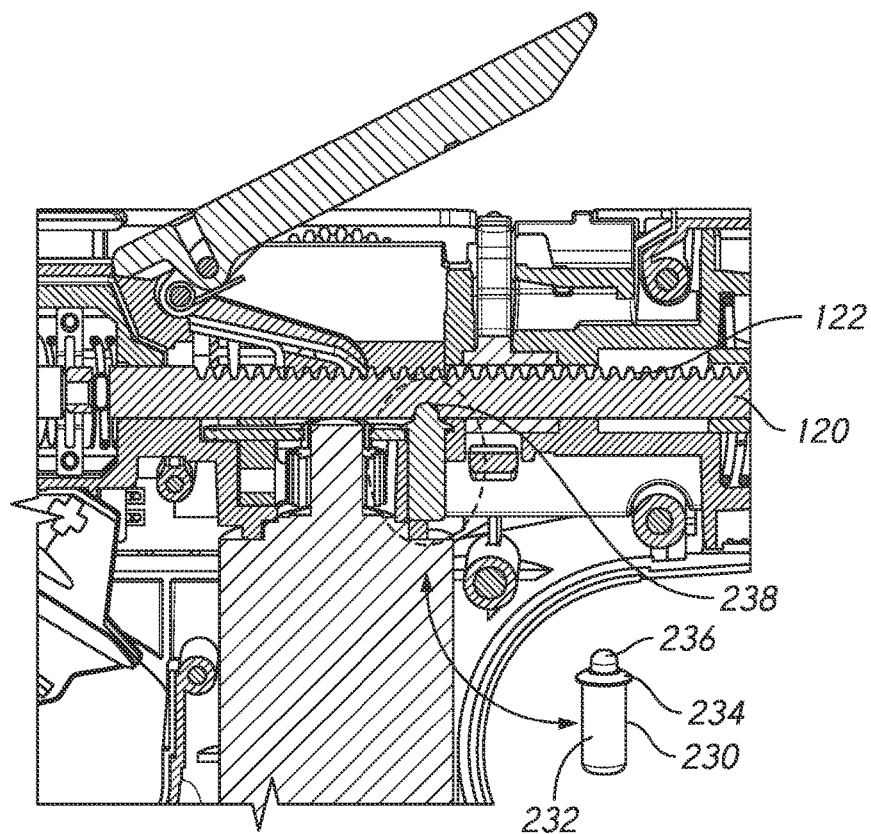
FIG. 20 is a cut-away side view of a powered handle assembly with another embodiment of retention mechanism.

With reference to FIG. 20, certain aspects of an embodiment of retention mechanism for a manual return mechanism are illustrated. The retention mechanism comprises a plunger 230 biased to engage the actuation shaft of the handle assembly when the manual return mechanism has been actuated. In certain embodiments, the plunger 230 is biased by a spring 232 positioned to bias a tip of the plunger towards the actuation shaft 120. In certain embodiments, the plunger 230 can be disposed in a location in the handle assembly such that it is spaced apart from an outer surface of the actuation shaft 120 with the actuation shaft oriented for powered operation. For example, the plunger 230 can be positioned in the recess in the outer surface of the actuation shaft 120 with the actuation shaft oriented for powered operation. In certain embodiments, the plunger 230 can have a radiused or ball tip 236 such that the radiused tip can engage an outer surface of the actuation shaft 120 oriented for powered operation without the radiused tip imparting an undesirable frictional force to the actuation shaft. In certain embodiments, the ball tip 236 of the plunger 230 can directly engage an outer surface of the actuation shaft. In certain embodiments, the actuation shaft 120 can comprise a groove or dimple 238 positioned to engage the plunger 230 with the actuation shaft 120 oriented for actuation of the manual return mechanism and the actuation shaft 120 proximally retracted. For example, in certain embodiments, the dimple 238 can be disposed at a location generally diametrically opposed to the rack 122 of the actuation shaft 120. Thus, in embodiments of retention mechanism including a ball or radiused tip plunger, the plunger 230 can engage the dimple 238 of the actuation shaft 120 in a positive detent engagement to retain the actuation shaft 120 within the handle assembly.

Figure 21:
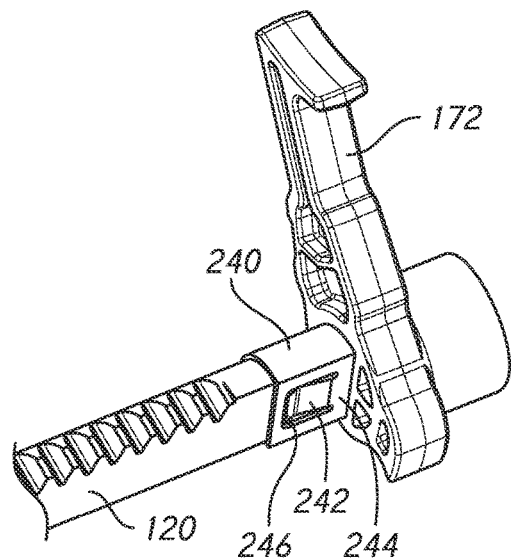
FIG. 21 is a perspective view of another embodiment of retention mechanism disposed on an embodiment of actuation shaft.
Figure 22:
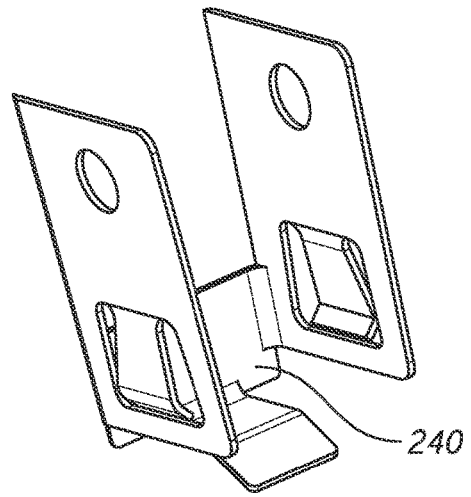
FIG. 22 is a perspective view of the retention mechanism of FIG. 21.

With reference to FIGS. 21-22, certain aspects of an embodiment of retention mechanism for a manual return mechanism are illustrated. The illustrated embodiment of retention mechanism includes a cantilever member arranged and configured to apply a frictional force to the actuation shaft. In certain embodiments, the retention mechanism can comprise a spring body 240 mountable to the handle assembly. The spring body 240 can comprise a metal material or a plastic material having a cantilever member 242 extending therefrom in a leaf spring like fashion. The cantilever member can have a fixed end 244 connected to the spring body 240 and a contact end 246 opposite the fixed end 244. The contact end 246 is arranged to apply a contact force to the actuation shaft 120. The cantilever member 242 is configured to apply a first frictional force to the actuation shaft when the actuation shaft 120 is retracted in a proximal direction and a second frictional force greater than the first frictional force when the actuation shaft 120 is moved distally. For example, in some embodiments, the fixed end 244 can be positioned distal the contact end 246 to provide direction dependent friction forces that tend to be higher when the actuation shaft is moved in a distal direction than when the actuation shaft is moved in a proximal direction. The friction forces applied by the cantilever member can be sufficient to retain the rack of the actuation shaft while only applying a relatively small, tolerable load to the drive system.

With reference to FIG. 21, in some embodiments, the spring body 240 can be positioned partially or completely surrounding a portion of the actuation shaft 120. The spring body 240 can have a cantilever member 242 extending radially inwardly from a fixed end 244 to a contact end 246 to slidingly engage the actuation shaft 120, generating a frictional force thereon. In the illustrated embodiment, the spring body 240 is positioned to abut the rotation lever 172 of the manual return mechanism. In other embodiments, the spring body 240 can be positioned at other locations within the handle assembly.

With reference to FIG. 22, in some embodiments, a spring body 240 can be formed of a sheet of a metallic or plastic material. The sheet of material can have one or a plurality of cantilever members formed therewith and biased in a leaf spring like fashion to slidingly engage the actuation shaft of a handle assembly. In certain embodiments, a cantilever member can be positioned to engage the rack of the actuation shaft 120 to engage the actuation shaft 120 in a ratchet like fashion such that only a small frictional force is generated by the spring body when the actuation shaft 120 is moved in a proximal direction, but a cantilever member engages the rack on the actuation shaft 120 when the actuation shaft is moved in a distal direction.

Figure 23:
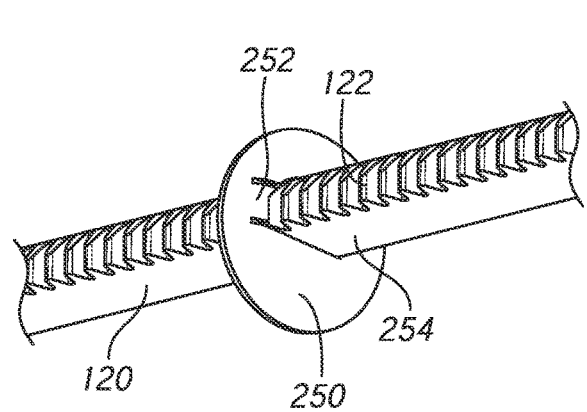
FIG. 23 is a perspective view of another embodiment of retention mechanism disposed on an embodiment of actuation shaft.
Figure 24:
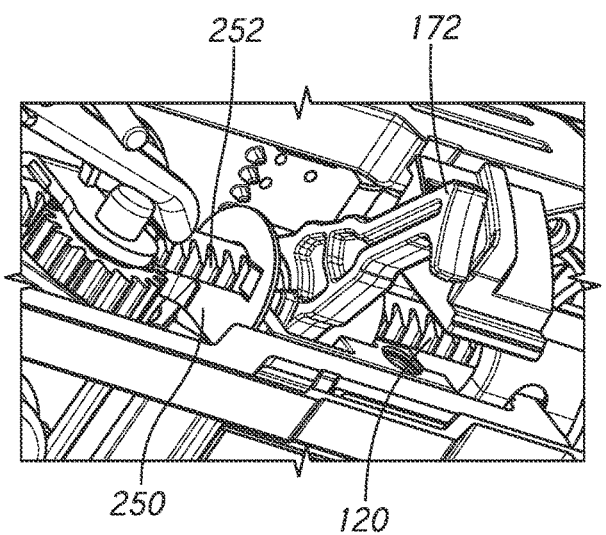
FIG. 24 is a cut-away perspective view of the retention mechanism of FIG. 23 in an embodiment of actuation mechanism of a powered handle.

With reference to FIGS. 23-24, certain aspects of an embodiment of retention mechanism for a manual return mechanism are illustrated. In the illustrated embodiment, the retention mechanism comprises a keeper disc 250. The keeper disc 250 can comprise a flap 252 or strip of material that rests in engagement with the rack 122 of the actuation shaft 120 to prevent unintentional longitudinal movement of the rack. In certain embodiments, the keeper disc 250 comprises a sheet of material having an aperture 254 therethrough through which the actuation shaft extends. The flap 252 or strip of material can extend adjacent the aperture 254 to engage the rack 122 of the actuation shaft 120. The keeper disc 250 can be formed of a flexible material such that a force to bend the flap 252 or strip of material is relatively small, allowing actuation of the rack in powered operation and upon actuation of the manual return mechanism. In certain embodiments, the keeper disc 250 can surround or encapsulate the actuation shaft 120. In certain embodiments, the keeper disc 250 can be attached to an internal component of the handle assembly. For example, in certain embodiments, the keeper disc 250 can be attached to a support housing for the actuation shaft 120. In other embodiments, the keeper disc can be attached to the rotation lever 172 of the manual return mechanism.

Figure 25:
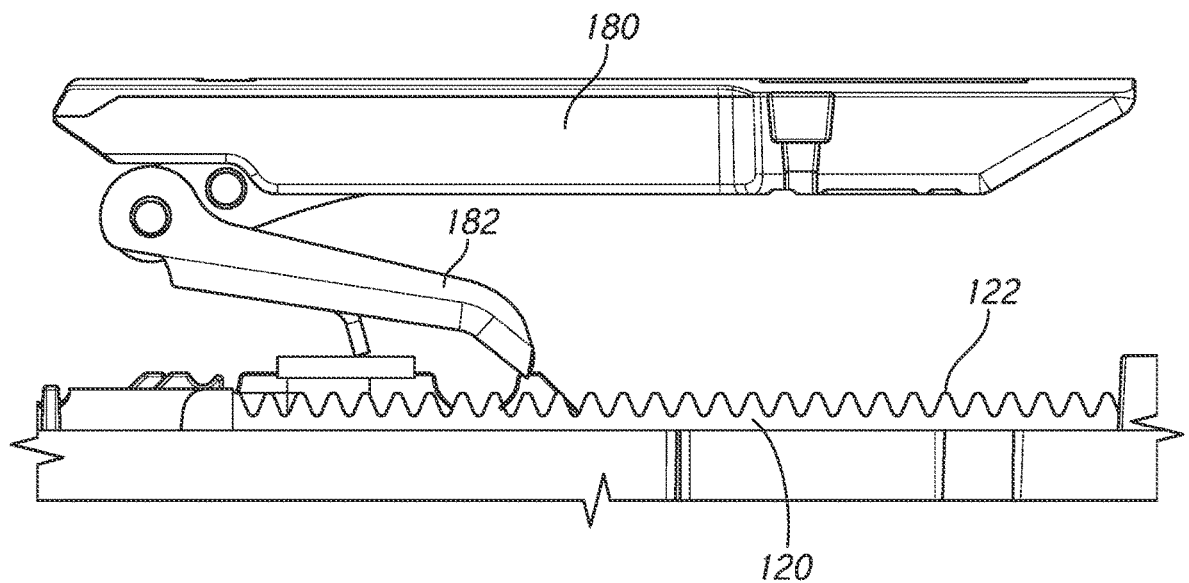
FIG. 25 is a side view of an embodiment of override return mechanism in a disengaged configuration.
Figure 26:
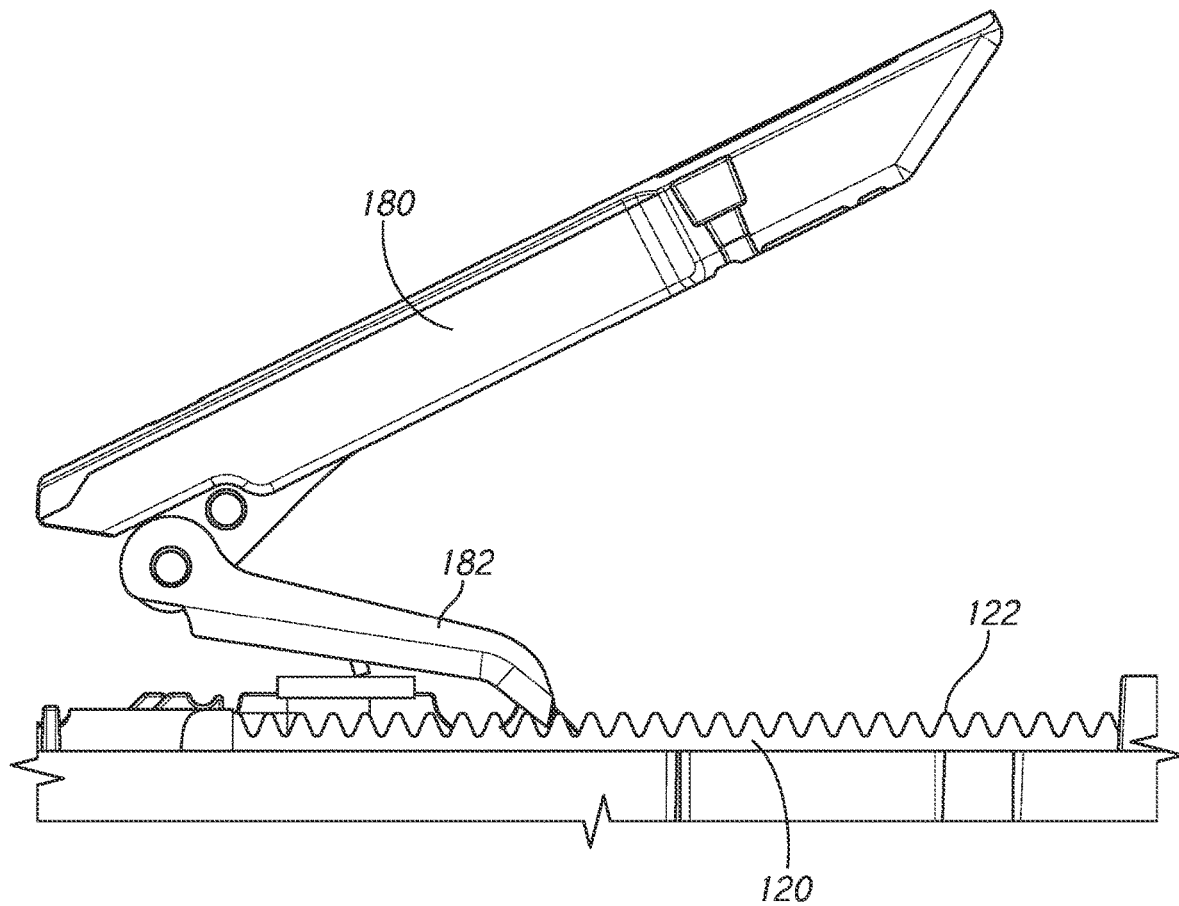
FIG. 26 is a side view the override return mechanism of FIG. 25 in a return configuration.
Figure 27:
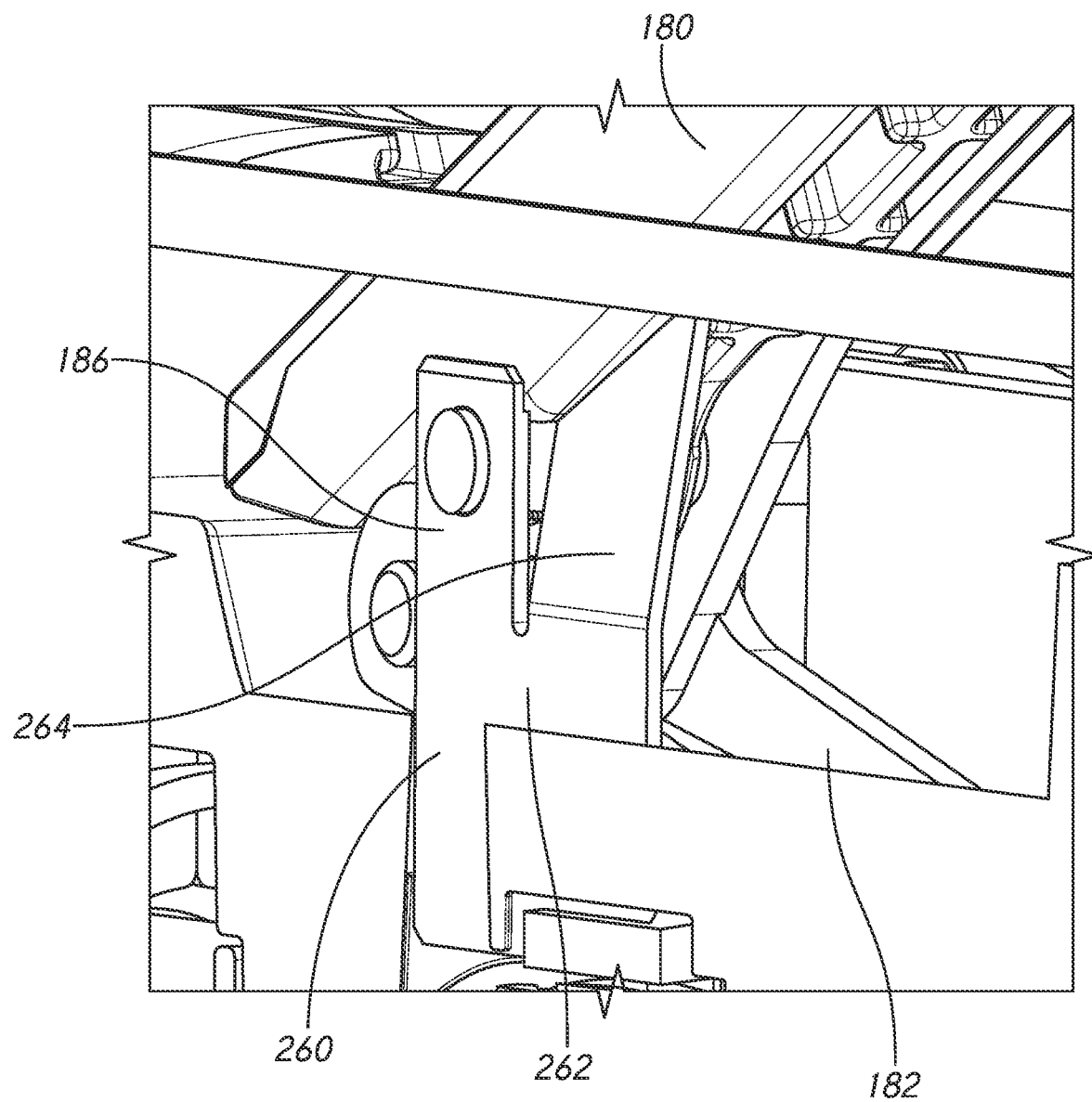
FIG. 27 is a detail perspective view another embodiment of retention mechanism positioned on an override return mechanism of FIG. 25.

With reference to FIGS. 25-27, certain aspects of an embodiment of retention mechanism for a manual return mechanism are illustrated. FIG. 25 illustrates the manual return mechanism and actuation shaft 120 in a first position with the return lever 182 adjacent the handle assembly. FIG. 26 illustrates the manual return mechanism and actuation shaft 120 with the return lever 182 in a second position spaced apart from the handle assembly. As discussed with reference to FIGS. 10-11, a user can cycle the return lever 180 of the manual return mechanism between the first position and the second position to retract the actuation shaft 120 proximally through interaction of the return pawl 182 with the rack 122. When the manual return mechanism is in the second position, the return pawl 182 is maintained in engagement with the rack 122 of the actuation shaft 120. With the return pawl 182 engaged with the rack 122 of the actuation shaft 120, the actuation shaft 120 can be prevented from unintentional longitudinal advancement. Accordingly, in certain embodiments, a retention mechanism can be arranged and configured to maintain the pawl of the manual return mechanism in engagement with the rack of the actuation shaft following operation of the manual return mechanism to return the actuation rack to a proximal position.

With reference to FIG. 27, certain aspects of an embodiment of retention mechanism for a manual return mechanism are illustrated. In the illustrated embodiment, the retention mechanism comprises a leaf spring assembly 260. The leaf spring assembly 260 can comprise a bracket 262 and a spring arm 264 extending from the bracket 262. The bracket 262 can be coupled to the manual return mechanism at a pivot joint 186 for the return lever 180 such that the spring arm 264 contacts a lower surface of the return lever 180 and biases the lever away from the handle assembly upon actuation of the manual return mechanism. Thus, the return lever 180 is biased to maintain the return pawl 182 of the manual return mechanism in contact with the rack 122 of the actuation shaft 120 to prevent unintentional movement of the actuation shaft 120. In other embodiments, other spring arrangements can be used to bias the return pawl 182 into engagement with the rack 122 of the actuation shaft 120.

Figure 28:
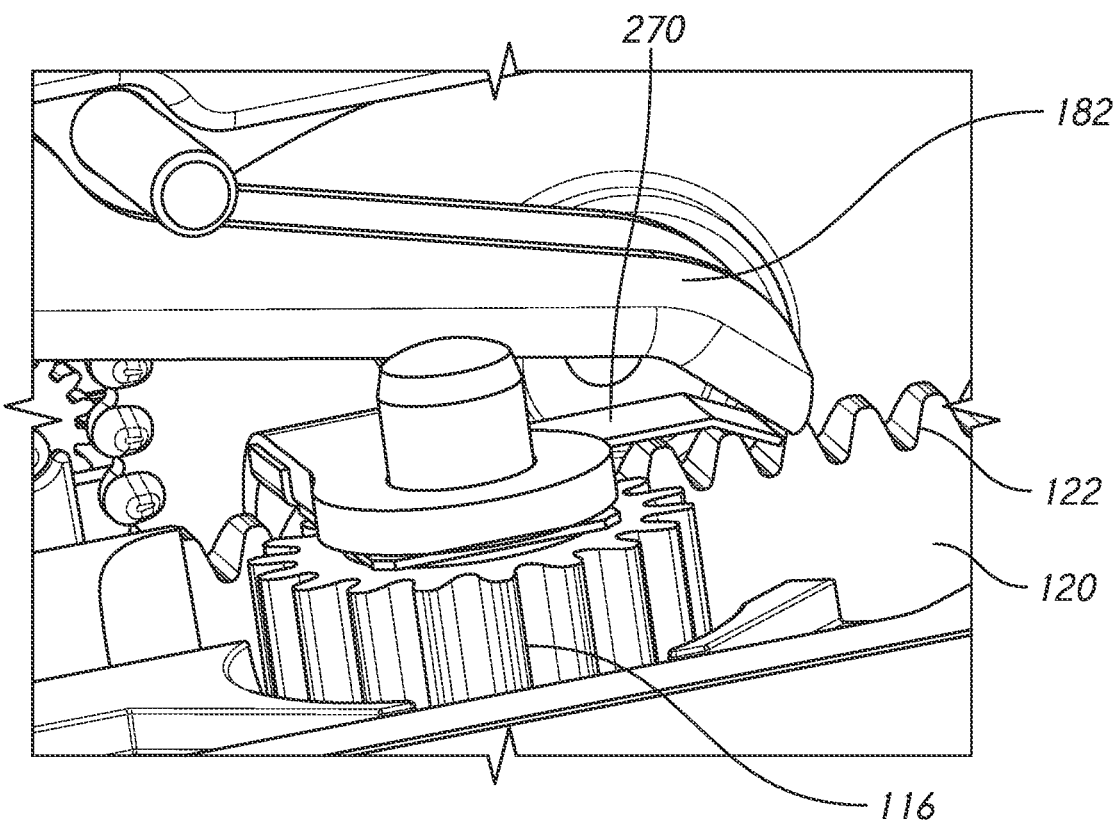
FIG. 28 is a cut-away perspective view of an embodiment of override return mechanism with another embodiment of retention mechanism.
Figure 29:
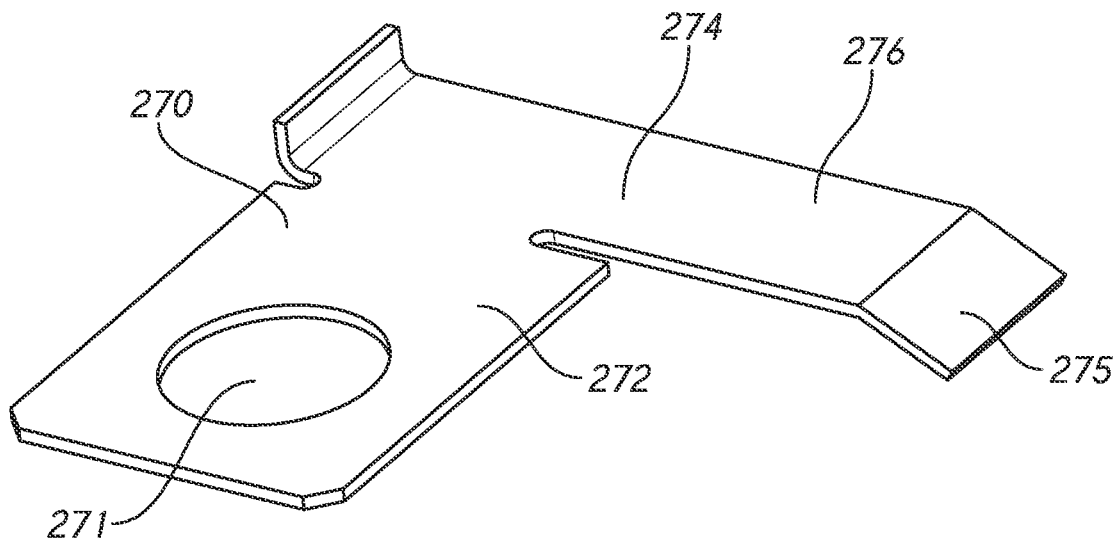
FIG. 29 is a perspective view of the retention mechanism of FIG. 28.

With reference to FIGS. 28-29, certain aspects of an embodiment of retention mechanism for a manual return mechanism are illustrated. The retention mechanism can comprise a rack pawl 270 engageable with the rack 122 of the actuation shaft 120 when the actuation shaft 120 is oriented for actuation with the manual return mechanism. In the illustrated embodiment, the rack pawl 270 comprises a bracket 272 positionable adjacent the actuation shaft 120 and a pawl 274 extending form the bracket 272. As illustrated, the bracket 272 comprises an aperture 271 mountable on the auxiliary gear 116 of the drive system of the handle assembly. Thus, in the illustrated embodiment, the rack pawl 270 is out of engagement with the rack 122 of the actuation shaft 120 when the actuation shaft is oriented for powered operation and the rack pawl engages the rack of the actuation shaft with the actuation shaft oriented for operation of the manual return mechanism. In other embodiments, a bracket can be configured to be disposed on other components or elsewhere within the handle assembly.

With continued reference to FIGS. 28-29, the pawl 274 of the rack pawl 270 can be positioned to engage the rack 122 of the actuation shaft 120 with the actuation shaft 120 oriented for operation of the manual return mechanism. Upon rotation of the actuation shaft 120 to the orientation for operation of the manual return mechanism, the pawl 274 can desirably be configured to allow proximal retraction of the actuation shaft 120 relative to the handle assembly and restrict distal advancement of the actuation shaft 120. In certain embodiments, the pawl 274 can comprise a pawl tooth 275 disposed at the end of a flexible cantilever arm 276 extending from the bracket 272. The pawl tooth 275 can be angled to allow movement of the actuation shaft in the proximal direction and restrict movement of the actuation shaft in the distal direction relative to the handle assembly. The pawl tooth 275 of the pawl 274 of the retention mechanism can remain engaged with the rack 122 of the actuation shaft regardless of whether the return pawl 182 of the manual return mechanism is engaged with the rack 122.

Figure 30:
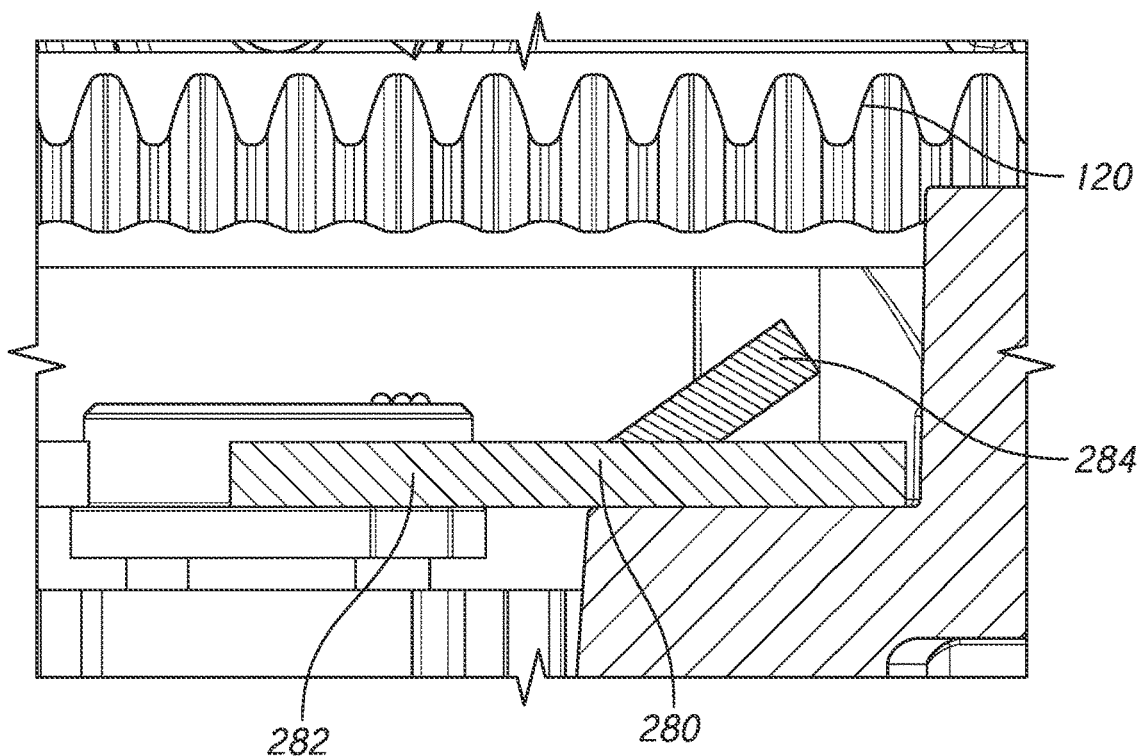
FIG. 30 is a cut-away side view of an embodiment of actuation mechanism of a powered handle with another embodiment of retention mechanism with the actuation shaft oriented for powered operation of the powered handle.
Figure 31:
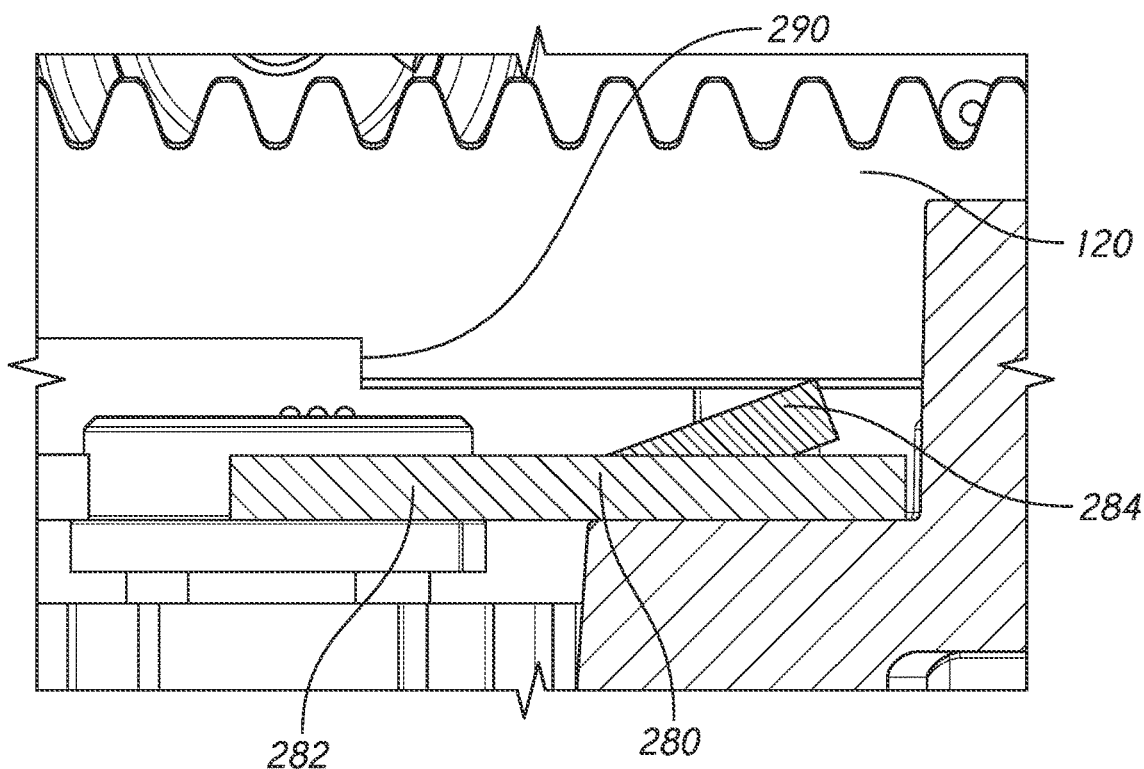
FIG. 31 is a cut-away side view of the actuation mechanism of FIG. 30 with the actuation shaft oriented for operation with a manual return mechanism.
Figure 32:
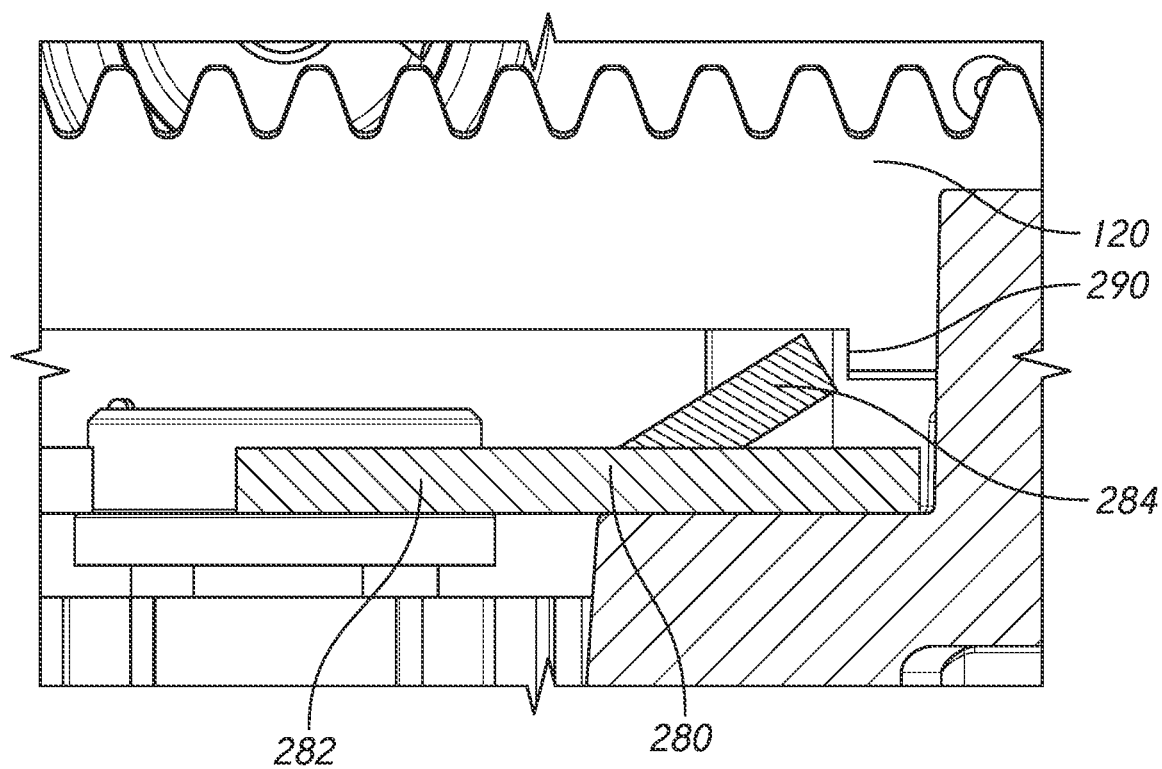
FIG. 32 is a cut-away side view of the actuation mechanism of FIG. 30 with the retention mechanism retaining longitudinal movement of the actuation shaft.

With reference to FIGS. 30-32, certain aspects of an embodiment of retention mechanism for a manual return mechanism are illustrated. In certain embodiments, the retention mechanism can comprise a catch assembly 280 arranged and configured to engage a portion of the actuation shaft 120 to restrain distal longitudinal movement of the actuation shaft following retraction of the actuation shaft by the manual return mechanism. FIG. 30 illustrates a detail side view of the actuation shaft 120 and catch assembly 280 with the actuation shaft 120 in an orientation for powered operation of the handle assembly. When the actuation shaft 120 is oriented for powered operation of the actuation shaft 120, the catch assembly 280 is out of contact with the actuation shaft 120. For example, in the illustrated embodiment, the catch assembly 280 can be positioned in the handle assembly to be aligned with the recess of the actuation shaft 120 when the actuation shaft 120 is oriented for powered operation of the handle assembly. FIGS. 31-32 illustrate a detail side view of the actuation shaft 120 and catch assembly 280 with the actuation shaft 120 in an orientation for retraction with the manual return mechanism and in a partially retracted position (FIG. 31) and a fully retracted position (FIG. 32).

With continued reference to FIGS. 30-32, The catch assembly 280 can comprise a mount plate or bracket 282 having a catch lever 284 extending therefrom. The bracket 282 can be mounted to a support housing of the handle assembly or other components positioned therein. In other embodiments, the catch assembly 280 can comprise a catch lever 284 directly mounted to or integrally formed with a support housing of the handle assembly. For example, in various embodiments, the catch assembly 280 can be mounted to or integrally formed with a top support of the handle assembly, or a top or bottom housing portion of the handle assembly. In various embodiments, the catch assembly 280 can comprise a metal or plastic material.

With reference to FIGS. 31-32, the actuation shaft 120 can comprise a recess or catch tooth 290 formed therein. In the illustrated embodiment, the actuation shaft comprises a recess having a single proximal edge or catch tooth 290. In other embodiments, it is contemplated that the actuation shaft can comprise more than one catch tooth positioned to be engaged by the catch lever at various longitudinal positions of the actuation shaft.

With continued reference to FIGS. 31-32, when the actuation shaft 120 is oriented for operation of the manual return mechanism, during retraction of the actuation shaft 120, the catch lever 284 contacts and slidingly engages an outer surface of the actuation shaft 120. As illustrated, the recess and catch tooth 290 are positioned on the actuation shaft 120 such that when the actuation shaft is oriented for operation of the manual return mechanism and proximally retracted, the catch lever 284 engages the catch tooth 290. With the catch lever 284 engaged with the catch tooth 290, upon distal movement of the actuation shaft 120 relative to the handle assembly the catch lever 284 engages the catch tooth 290 of the recess to restrain the actuation shaft 120 from further distal movement. The catch lever 284 can be formed of a flexible material that is biased towards the actuation shaft 120 such that once it engages the recess of the actuation shaft 120, the catch lever 284 is biased towards a recessed surface of the recess.

Figure 33:
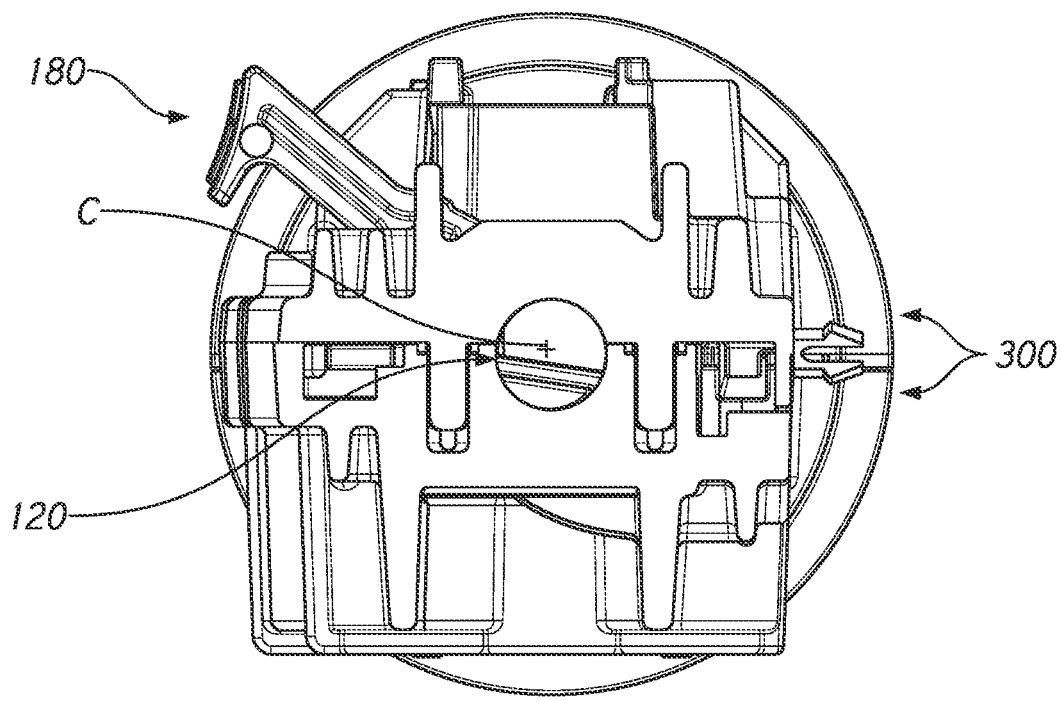
FIG. 33 is a cross-sectional end view of an embodiment of actuation mechanism of a powered handle with an override return mechanism in a disengaged configuration.
Figure 34:
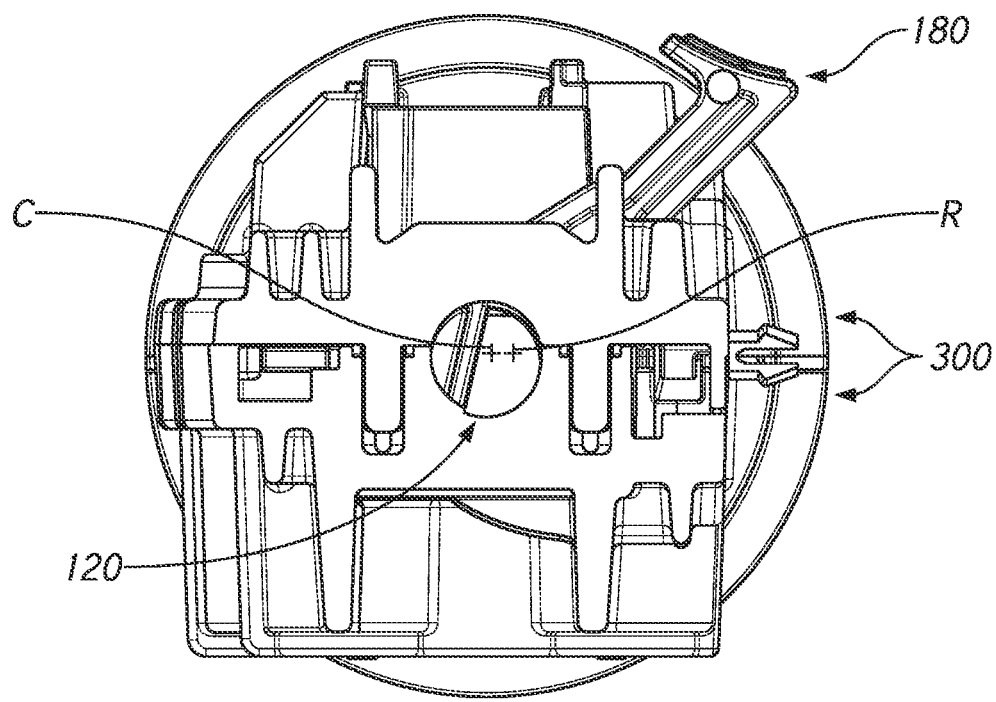
FIG. 34 is a cross-sectional end view of the actuation mechanism of FIG. 32 with the override return mechanism in a return configuration.
Figure 35:
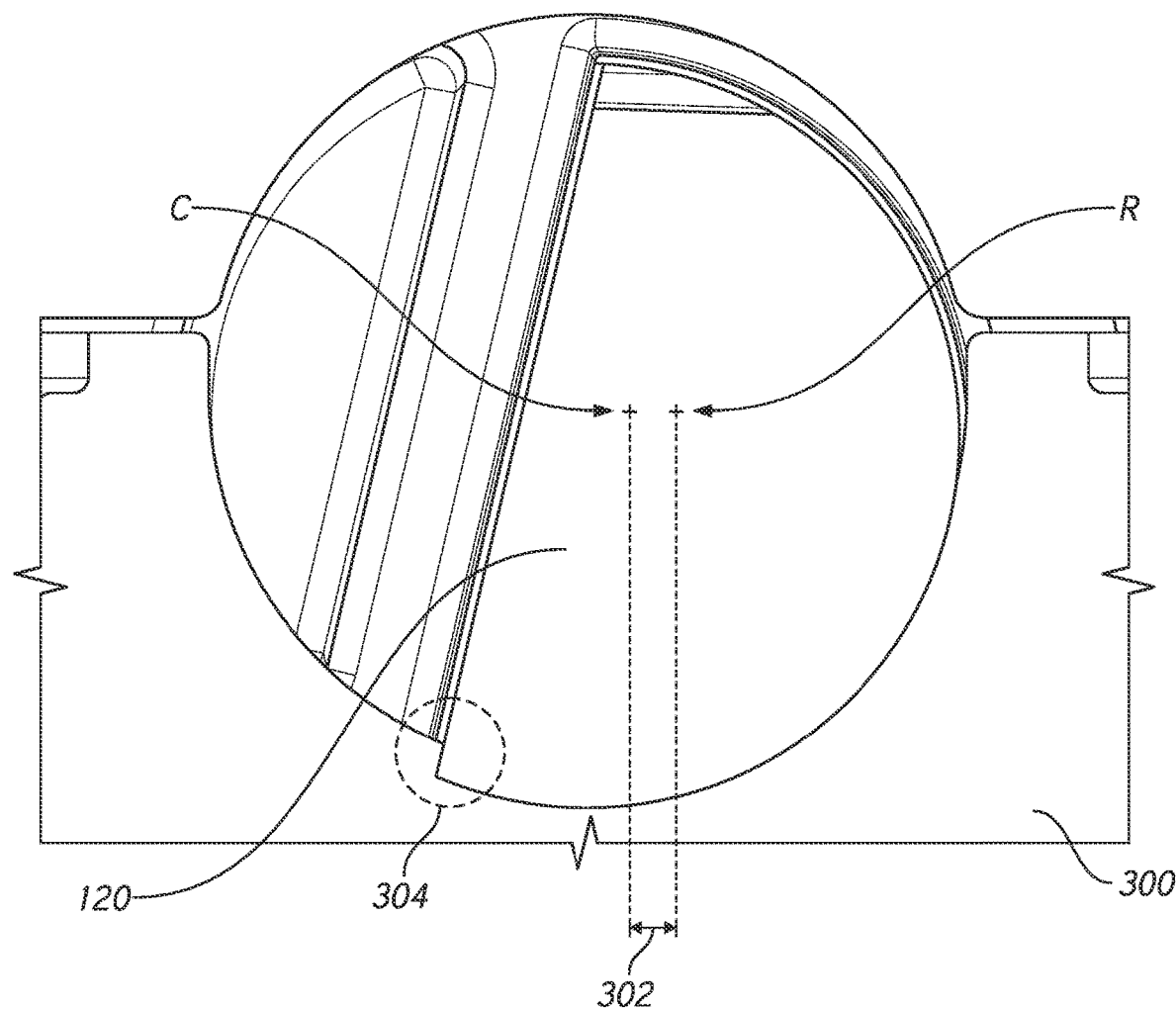
FIG. 35 is a detail view of the override return mechanism of FIG. 32 in a return configuration.

With reference to FIGS. 33-35, certain aspects of an embodiment of retention mechanism for a manual return mechanism are illustrated. In the illustrated embodiment, the retention mechanism can be integrated with the manual return mechanism such that when the actuation shaft is oriented for operation by the manual return mechanism, a friction force is applied to the actuation shaft to oppose longitudinal movement thereof. This frictional force restrains the actuation shaft from distal movement following operation of the manual return mechanism. The illustrated embodiment of retention mechanism is configured to only apply the described frictional force with the actuation shaft 120 oriented to be returned by the manual return mechanism (FIG. 34), without adding additional load when the actuation shaft 120 is oriented for powered operation (FIG. 33). In certain embodiments, the retention mechanism can be incorporated in the manual return mechanism by offsetting a rotational axis of the manual return mechanism from a longitudinal axis of the actuation shaft with the actuation shaft oriented for powered operation.

With reference to FIG. 33, with the actuation shaft 120 oriented for powered operation, the actuation shaft 120 is aligned with a central axis C of the support housing or drivetrain enclosure 300. Thus, in this orientation, the actuation shaft 120 can be longitudinally driven by the powered drive system without a frictional force being applied by the retention mechanism.

With reference to FIG. 34, as the actuation shaft 120 is rotated to the orientation for operation of the manual return mechanism, an offset between a rotation axis R of the rotation lever 180 and a central axis of the support housing or drivetrain enclosure 300 forces the actuation shaft into a surface of the support housing or drive enclosure as shown in FIG. 35. Accordingly, with the actuation shaft oriented for operation of the manual return mechanism, the actuation shaft slidingly engages a surface of the support housing or drive enclosure. This sliding engagement can prevent unintentional distal movement of the actuation shaft during and following operation of the manual return mechanism. The illustrated embodiment includes a retention mechanism comprising an offset 302 between the axis of rotation of the actuation shaft during operation of the manual return mechanism to generate frictional forces at an engagement region 304 between the actuation shaft and the support housing with the actuation shaft oriented for operation of the manual return mechanism. It is contemplated that in other embodiments, a retention mechanism can be arranged to apply a friction force to the actuation shaft in an orientation for operation of the manual return mechanism can be accomplished through use of cam surfaces within the drivetrain enclosure and the rotation lever.

Figure 36:
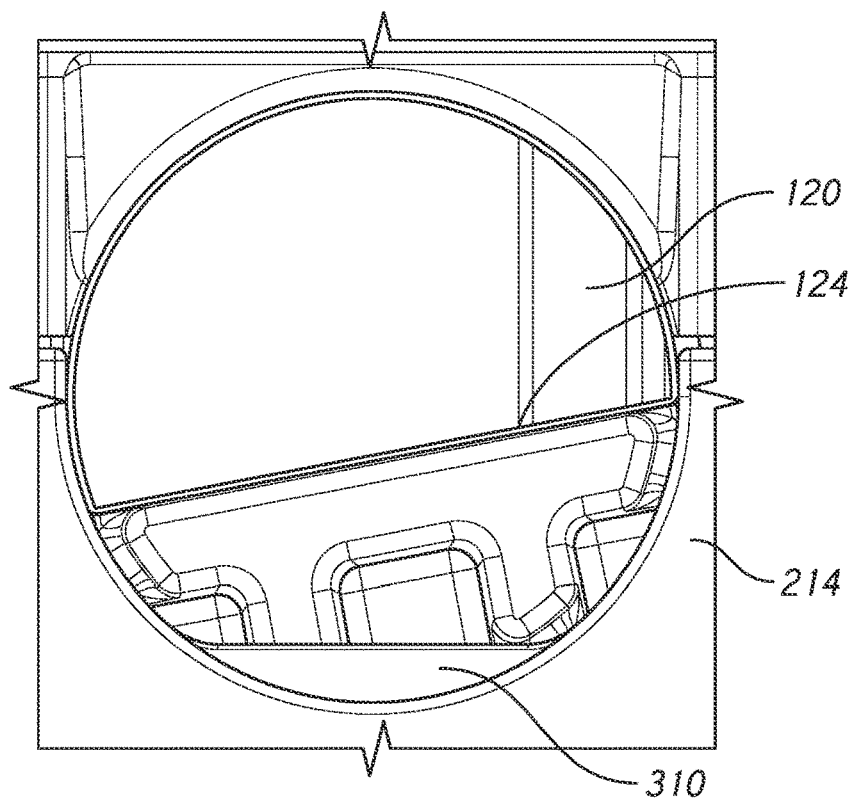
FIG. 36 is a cross-sectional end view of an embodiment of actuation mechanism of a powered handle in a disengaged configuration.
Figure 37:
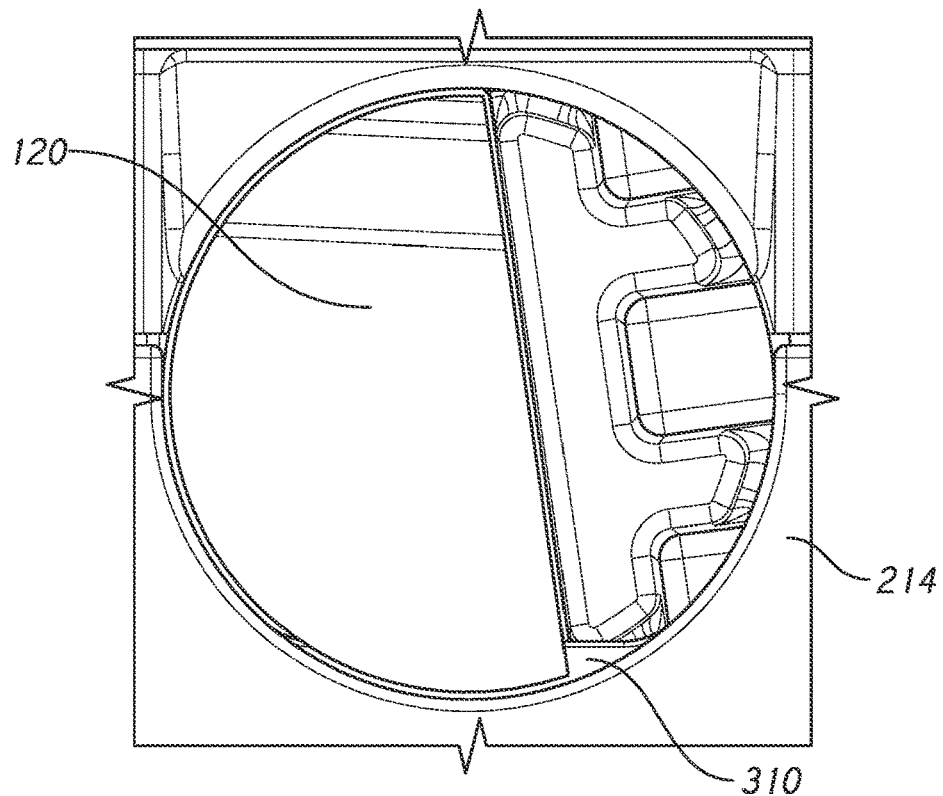
FIG. 37 is a cross-sectional end view of an embodiment of actuation mechanism of a powered handle in a return configuration.

With reference to FIGS. 36-40, certain aspects of embodiments of retention mechanism for a manual return mechanism are illustrated. These embodiments are arranged to generate a normal force perpendicular to the longitudinal axis of the actuation shaft upon actuation of the manual return mechanism, similar to embodiments of retention mechanism having an offset rotational axis, as discussed with reference to FIGS. 33-35. As illustrated in FIGS. 36-40, a mechanical interference is employed such that, once the actuation shaft 120 is rotated for operation of the manual return mechanism, the rack component engages a crush feature 310 within the handle assembly such that the actuation shaft cannot be expelled under its own weight. Desirably, the crush feature 310 is positioned within the handle assembly such that it is spaced apart from the actuation shaft 120 during powered operation. Accordingly, as illustrated in FIG. 36 in some embodiments, the crush feature is positioned to be aligned with the recess 124 of the actuation shaft 120 with the actuation shaft 120 oriented for powered operation. When the actuation shaft 120 is rotated for operation by the manual return mechanism, the actuation shaft 120 slidingly engages the crush feature 310 (FIG. 37).

Figure 38:
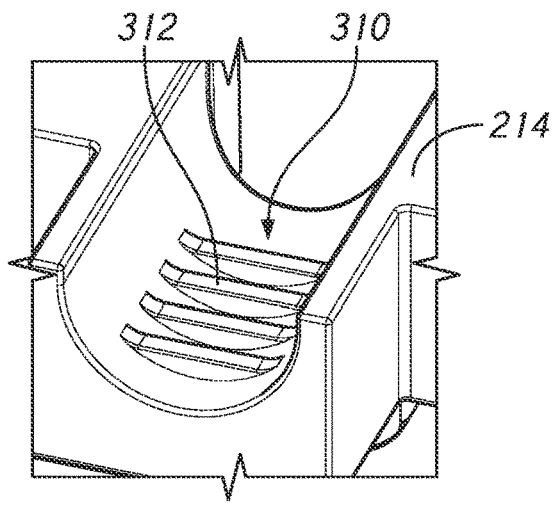
FIG. 38 is a detailed perspective view of an embodiment of retention mechanism for the actuation mechanism of FIG. 35.
Figure 39:
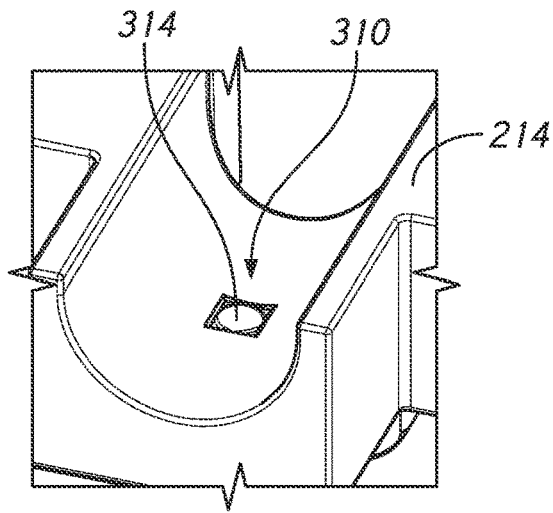
FIG. 39 is a detailed perspective view of another embodiment of retention mechanism for the actuation mechanism of FIG. 35.
Figure 40:
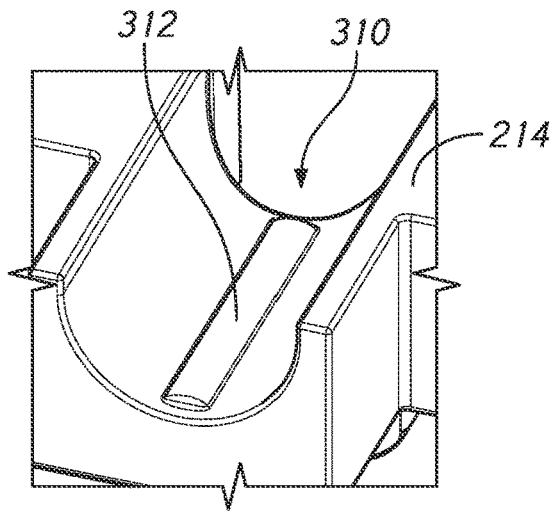
FIG. 40 is a detailed perspective view of another embodiment of retention mechanism for the actuation mechanism of FIG. 35.

With reference to FIGS. 38-40, in various embodiments, a crush feature 310 positioned within the handle assembly can take on a number of configurations. For example, as illustrated in FIG. 38, in certain embodiments, the crush feature 310 can comprise one or more ribs 312 extending transversely to a longitudinal axis of the actuation shaft. The one or more ribs 312 can be positioned in a support housing 214 of the actuation shaft. As shown in FIG. 39, in some embodiments, the crush feature 310 can comprise a compressible hemispheric protrusion 314. In other embodiments, as illustrated in FIG. 40, the crush feature 310 can comprise one or more ribs 316 extending longitudinally within the support housing 214. In certain embodiments, it is contemplated that the crush feature comprises a rubber material. While FIGS. 38-40 illustrate various protrusions and ribs extending from a portion of the support housing 214 within the handle assembly, it is contemplated that in other embodiments, similar features can be implemented within other mating components or as separate components within the handle assembly.

Figure 41:
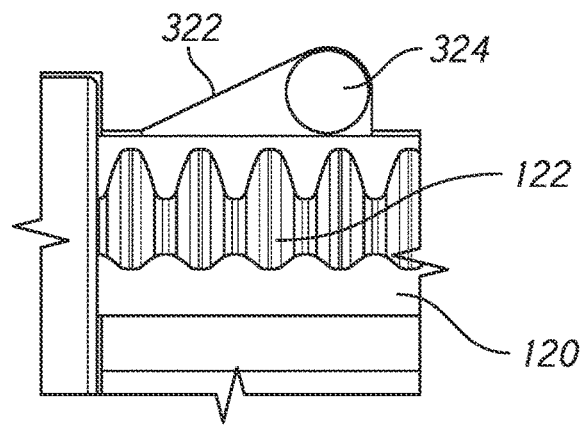
FIG. 41 is a detailed side view of another embodiment of retention mechanism for an actuation mechanism of powered handle with an override return mechanism in a disengaged configuration.
Figure 42:
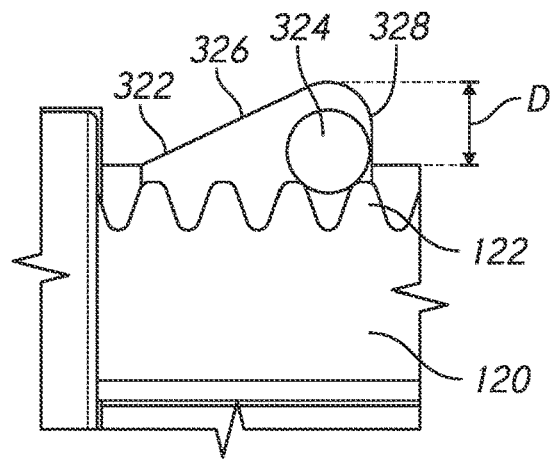
FIG. 42 is a detailed side view of the retention mechanism of FIG. 40 with the override return mechanism in a return configuration.
Figure 43:
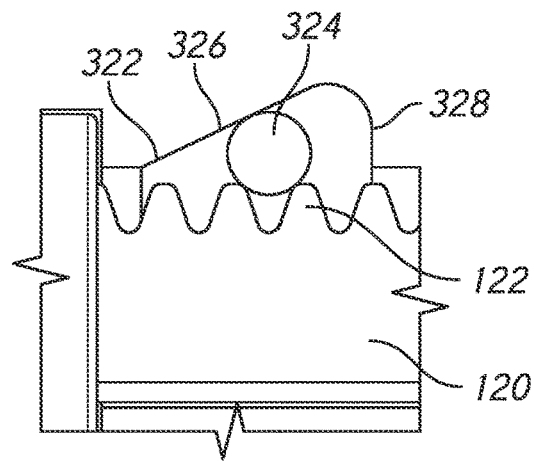
FIG. 43 is a detailed side view of the retention mechanism of FIG. 40 with the retention mechanism engaging the actuation shaft.

With reference to FIGS. 41-43, certain aspects of an embodiment of retention mechanism for a manual return mechanism are illustrated. In the illustrated embodiment, the retention mechanism comprises a one-way wedge locking assembly 320 having a ramped or wedge locking recess 322 and a lock member 324. The locking recess 322 can be formed in a support housing or another handle assembly component adjacent the actuation shaft. As illustrated in FIG. 41, with the actuation shaft 120 oriented for powered operation, the lock member 324 is positioned within the locking recess 322 adjacent a smooth outer surface of the actuation shaft 120 offset from the rack 122. In the illustrated embodiment, the lock member 324 can comprise a ball bearing such that during powered operation it rolls smoothly along the surface of the actuation shaft 120. In other embodiments, the lock member 324 can comprise a pin or another sliding or rolling member that can move smoothly along an outer surface of the actuation shaft 120. With reference to FIGS. 42-43, when the actuation shaft 120 is rotated to the orientation for operation of the manual return mechanism, the lock member 324 is positioned in the rack 122 of the actuation shaft 120. The lock recess 322 comprises a tapered, ramped, or wedged sidewall 326 positioned such that upon distal advancement of the actuation shaft 120 relative to the handle assembly, the lock member 324 engages the rack 122 and the sidewall 326 to arrest further distal movement of the actuation shaft. The lock recess 322 can further comprise a second sidewall 328 opposite the wedged sidewall and a depth D at the second sidewall 328. In certain embodiments, the lock recess 322 is sized such that the depth D at the second sidewall 328 allows the lock member 324 to be moved along the rack 122 of the actuation shaft 120 as the actuation shaft 120 is moved proximally with respect to the handle assembly.

In certain embodiments, a damping grease can be applied to the actuation shaft of the handle assemblies described herein to enhance a friction force or drag on the actuation shaft. In some embodiments, a damping grease can be applied in addition to one of the retention mechanisms described in FIGS. 14-42. In other embodiments, a damping grease can be applied to one or more components of the handle assembly having no additional retention mechanism to create drag on the actuation shaft during operation of the manual return mechanism to reduce the likelihood of unintentional movement of the actuation shaft during operation of the manual return mechanism. The viscosity and placement of the damping grease can be selected for desired operation of the actuation shaft. For example, a relatively heavy grade of damping grease liberally applied to sliding surfaces of the actuation shaft can retain the actuation shaft within the handle assembly for a relatively longer time, but can also require more effort from a user in operation of the manual return mechanism due to drag on the actuation shaft. In contrast, a relatively light grade of damping grease with targeted application can create a relatively small drag on the actuation shaft during operation of the manual return mechanism but can prevent unintentional movement of the actuation shaft within the handle assembly for a relatively shorter period of time. In certain embodiments, a viscosity of the damping grease can be selected such that the actuation shaft will be retained within the handle assembly indefinitely with the actuation shaft oriented for operation of the manual return mechanism.

In certain embodiments, the retention mechanism can comprise a rubber grommet or ring that can apply a frictional force to the actuation shaft to prevent unintended movement of the actuation shaft. In some embodiments, a rubber ring, pad, or surface can be included in one of the retention mechanisms described in FIGS. 14-42 to apply a frictional force to the actuation shaft.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A handle assembly for a surgical stapler, the handle assembly comprising:
   a handle body, the handle body comprising a stationary handle and a trigger pivotably coupled to the handle body;
   an electric motor disposed within the handle body;
   an actuation shaft slidable within the handle body along a longitudinal axis and rotatable within the handle body about the longitudinal axis, the actuation shaft comprising a rack formed thereon;
   a mechanical return mechanism; and
   a retention mechanism configured to restrict distal longitudinal advancement of the actuation shaft upon actuation of the mechanical return mechanism;
   wherein the retention mechanism comprises a plurality of fins extending transversely to the longitudinal axis, the plurality of fins frictionally engaging the actuation shaft upon actuation of the mechanical return mechanism.

2. A handle assembly for a surgical stapler, the handle assembly comprising:
   a handle body, the handle body comprising a stationary handle and a trigger pivotably coupled to the handle body;
   an electric motor disposed within the handle body;
   an actuation shaft slidable within the handle body along a longitudinal axis and rotatable within the handle body about the longitudinal axis, the actuation shaft comprising a rack formed thereon;
   a mechanical return mechanism; and
   a retention mechanism configured to restrict distal longitudinal advancement of the actuation shaft upon actuation of the mechanical return mechanism;

wherein the retention mechanism comprises a plunger biased into frictional engagement with the actuation shaft upon actuation of the mechanical return mechanism.

3. The handle assembly of claim 2, wherein the actuation shaft comprises a groove sized and configured to receive the plunger to maintain the actuation shaft in a predetermined position.

4. A handle assembly for a surgical stapler, the handle assembly comprising:
 a handle body, the handle body comprising a stationary handle and a trigger pivotably coupled to the handle body;
 an electric motor disposed within the handle body;
 an actuation shaft slidable within the handle body along a longitudinal axis and rotatable within the handle body about the longitudinal axis, the actuation shaft comprising a rack formed thereon;
 a mechanical return mechanism; and
 a retention mechanism configured to restrict distal longitudinal advancement of the actuation shaft upon actuation of the mechanical return mechanism;
 wherein the retention mechanism comprises a leaf spring member engageable with the rack of the actuation shaft upon actuation of the mechanical return mechanism.

5. A handle assembly for a surgical stapler, the handle assembly comprising:
 a handle body, the handle body comprising a stationary handle and a trigger pivotably coupled to the handle body;
 an electric motor disposed within the handle body;
 an actuation shaft slidable within the handle body along a longitudinal axis and rotatable within the handle body about the longitudinal axis, the actuation shaft comprising a rack formed thereon;
 a mechanical return mechanism; and
 a retention mechanism configured to restrict distal longitudinal advancement of the actuation shaft upon actuation of the mechanical return mechanism;
 wherein the handle body comprises a crush element therein, the crush element positioned to engage with the actuation shaft upon actuation of the mechanical return mechanism.

6. A handle assembly for a surgical stapler, the handle assembly comprising:
 a handle body, the handle body comprising a stationary handle and a trigger pivotably coupled to the handle body;
 an electric motor disposed within the handle body;
 an actuation shaft slidable within the handle body along a longitudinal axis and rotatable within the handle body about the longitudinal axis, the actuation shaft comprising a rack formed thereon;
 a mechanical return mechanism; and
 a plurality of fins engageable with the actuation shaft upon actuation of the mechanical return mechanism, the plurality of fins extending transversely to the longitudinal axis to allow movement of the actuation shaft in a proximal direction and restrain the actuation shaft from movement in a distal direction.

7. The handle assembly of claim 6, wherein each fin of the plurality of fins extends at an angle within the range of approximately 30 degrees to approximately 75 degrees relative to the longitudinal axis.

8. The handle assembly of claim 7, wherein each fin of the plurality of fins extends at an angle of approximately 60 degrees relative to the longitudinal axis.

9. The handle assembly of claim 6, wherein the plurality of fins comprises two fins.

10. The handle assembly of claim 9, further comprising a gap extending between the two fins.

11. The handle assembly of claim 6, wherein the plurality of fins extends radially inwardly from the handle body.

12. The handle assembly of claim 6, wherein the actuation shaft is rotatable from a first position wherein the rack is operationally engaged with the electric motor to longitudinally slide the actuation shaft to a second position wherein the rack is disengaged from the electric motor and engaged with the manual return mechanism and engaged with the plurality of fins.

13. A handle assembly for a surgical stapler, the handle assembly comprising:
 a handle body, the handle body comprising a stationary handle and a trigger pivotably coupled to the handle body;
 an electric motor disposed within the handle body;
 an actuation shaft slidable within the handle body along a longitudinal axis and rotatable within the handle body about the longitudinal axis, the actuation shaft comprising a rack formed thereon;
 a mechanical return mechanism comprising a shaft rotation mechanism and a shaft retraction mechanism; and
 a retention mechanism configured to prevent distal longitudinal advancement of the actuation shaft upon actuation of the shaft retraction mechanism,
 wherein the actuation shaft is rotatable from a first position wherein the rack is operationally engaged with the electric motor to longitudinally slide the actuation shaft to a second position wherein the rack is disengaged from the electric motor and engaged with the manual return mechanism and engaged with the retention mechanism;
 wherein the retention mechanism comprises a featherboard element extending radially inwardly from the handle body and positioned out of alignment with the rack with the actuation shaft in the first position.

14. A handle assembly for a surgical stapler, the handle assembly comprising:
 a handle body, the handle body comprising a stationary handle and a trigger pivotably coupled to the handle body;
 an electric motor disposed within the handle body;
 an actuation shaft slidable within the handle body along a longitudinal axis and rotatable within the handle body about the longitudinal axis, the actuation shaft comprising a rack formed thereon;
 a mechanical return mechanism comprising a shaft rotation mechanism and a shaft retraction mechanism; and
 a retention mechanism configured to prevent distal longitudinal advancement of the actuation shaft upon actuation of the shaft retraction mechanism,
 wherein the actuation shaft is rotatable from a first position wherein the rack is operationally engaged with the electric motor to longitudinally slide the actuation shaft to a second position wherein the rack is disengaged from the electric motor and engaged with the manual return mechanism and engaged with the retention mechanism;
 wherein the retention mechanism comprises a crush element extending radially inwardly from the handle body, the crush feature positioned out of alignment with the actuation shaft with the actuation shaft in the first position, and the crush feature frictionally engageable with the actuation shaft with the actuation shaft in the second position.

15. The handle assembly of claim 14, wherein the crush element comprises a plurality of compressible ribs extending transversely to the longitudinal axis.

16. The handle assembly of claim 14, wherein the crush element comprises a compressible domed section.

17. The handle assembly of claim 14, wherein the crush element comprises a compressible longitudinal rib extending parallel to the longitudinal axis.

\* \* \* \* \*